United States Patent
Wingeier et al.

(10) Patent No.: US 11,097,097 B2
(45) Date of Patent: Aug. 24, 2021

(54) SYSTEM AMD METHOD FOR INDIVIDUALIZING NEUROMODULATION

(71) Applicant: Halo Neuro, Inc., San Francisco, CA (US)

(72) Inventors: Brett Wingeier, San Francisco, CA (US); Randall Lin, San Francisco, CA (US); Daniel Toker, San Francisco, CA (US)

(73) Assignee: Flow Neuroscience, Inc., Malmö (SE)

( * ) Notice: Subject to any disclaimer, the term of this patent is extended or adjusted under 35 U.S.C. 154(b) by 29 days.

(21) Appl. No.: 16/667,463

(22) Filed: Oct. 29, 2019

(65) Prior Publication Data

US 2020/0061375 A1 Feb. 27, 2020

Related U.S. Application Data

(63) Continuation of application No. 16/195,728, filed on Nov. 19, 2018, now Pat. No. 10,507,324.

(Continued)

(51) Int. Cl.
*A61N 1/08* (2006.01)
*A61N 1/20* (2006.01)
(Continued)

(52) U.S. Cl.
CPC .............. *A61N 1/08* (2013.01); *A61N 1/0456* (2013.01); *A61N 1/205* (2013.01); *A61N 1/3603* (2017.08);
(Continued)

(58) Field of Classification Search
CPC ........ A61N 1/08; A61N 1/0484; A61N 1/205; A61N 1/0452; A61N 1/0465;
(Continued)

(56) References Cited

U.S. PATENT DOCUMENTS

| | | |
|---|---|---|
| 3,472,233 A | 10/1969 | Sarbacher |
| 4,928,696 A | 5/1990 | Henderson et al. |

(Continued)

FOREIGN PATENT DOCUMENTS

| | | |
|---|---|---|
| CN | 103517732 A | 1/2014 |
| EP | 2449961 A1 | 5/2012 |

(Continued)

OTHER PUBLICATIONS

US 8,919,831, 07/2011, Tateishi et al. (withdrawn)

*Primary Examiner* — Paula J Stice
(74) *Attorney, Agent, or Firm* — Jeffrey Schox; Caitlin Ploch

(57) ABSTRACT

A system for individualizing neuromodulation includes a neurostimulation device having a set of electrodes, and an application executing on a user device. Additionally or alternatively, the system can include any or all of: a sensor system, a head-securing mechanism, a remote server, storage, an accessory device, and any other suitable component. A method for individualizing neuromodulation includes determining a task of interest to a user; determining a user skill level associated with the task; determining a set of goals; determining an individualized neuromodulation program comprising a neurostimulation pattern; and delivering the neurostimulation pattern to the user. Additionally or alternatively, the method can include any or all of: determining user progress; displaying user progress; receiving user feedback; determining and/or adapting neuromodulation program based on user progress and/or user feedback; and any other suitable process.

20 Claims, 14 Drawing Sheets

Related U.S. Application Data

(60) Provisional application No. 62/587,777, filed on Nov. 17, 2017.

(51) Int. Cl.
  *A61N 1/04* (2006.01)
  *A61N 1/36* (2006.01)
  *A61B 5/00* (2006.01)
  *A61B 5/16* (2006.01)
  *A61B 5/369* (2021.01)

(52) U.S. Cl.
  CPC .......... *A61N 1/36025* (2013.01); *A61B 5/16* (2013.01); *A61B 5/369* (2021.01); *A61B 5/6803* (2013.01); *A61B 5/7275* (2013.01); *A61N 1/0476* (2013.01); *A61N 1/0484* (2013.01)

(58) Field of Classification Search
  CPC .. A61N 1/0526; A61N 1/0529; A61N 1/0531; A61N 1/36014; A61N 1/36025; A61N 1/0479; A61M 21/02; A61M 2021/0072; A61M 2205/502
  See application file for complete search history.

(56) References Cited

U.S. PATENT DOCUMENTS

| | | |
|---|---|---|
| 4,967,038 A | 10/1990 | Gevins et al. |
| 4,977,895 A | 12/1990 | Tannenbaum |
| 5,058,605 A | 10/1991 | Slovak |
| 5,087,242 A | 2/1992 | Petelenz et al. |
| 5,137,817 A | 8/1992 | Busta et al. |
| 5,250,023 A | 10/1993 | Lee et al. |
| 5,387,231 A | 2/1995 | Sporer |
| 5,622,168 A | 4/1997 | Keusch et al. |
| 6,077,237 A | 6/2000 | Campbell et al. |
| 6,263,226 B1 | 7/2001 | Axelgaard et al. |
| 6,379,324 B1 | 4/2002 | Gartstein et al. |
| 6,406,811 B1 | 6/2002 | Hall et al. |
| 6,480,743 B1 | 11/2002 | Kirkpatrick et al. |
| 6,505,079 B1 | 1/2003 | Foster et al. |
| 6,510,333 B1 | 1/2003 | Licata et al. |
| 7,024,247 B2 | 4/2006 | Gliner et al. |
| 7,551,952 B2 | 6/2009 | Gevins et al. |
| 7,610,095 B2 | 10/2009 | Naisberg |
| 7,813,802 B2 | 10/2010 | Tcheng et al. |
| 7,818,515 B1 | 10/2010 | Umbehocker et al. |
| 7,828,947 B2 | 11/2010 | Oki et al. |
| 7,877,146 B2 | 1/2011 | Ansarinia et al. |
| 7,894,905 B2 | 2/2011 | John et al. |
| 7,966,073 B2 | 6/2011 | Pless et al. |
| 7,988,917 B2 | 8/2011 | Roesicke et al. |
| 8,116,875 B2 | 2/2012 | Osypka et al. |
| 8,121,694 B2 | 2/2012 | Molnar et al. |
| 8,195,174 B2 | 6/2012 | Lee et al. |
| 8,239,030 B1 | 8/2012 | Hagedorn et al. |
| 8,290,596 B2 | 10/2012 | Wei et al. |
| 8,301,265 B2 | 10/2012 | Starkebaum |
| 8,349,554 B2 | 1/2013 | Bahrami et al. |
| 8,380,316 B2 | 2/2013 | Hagedorn et al. |
| 8,419,716 B2 | 4/2013 | Weissenrieder-Norlin et al. |
| 8,473,063 B2 | 6/2013 | Gupta et al. |
| 8,554,324 B2 * | 10/2013 | Brocke .................. A61M 21/02 607/45 |
| 8,583,237 B2 | 11/2013 | Bedenbaugh |
| 8,591,392 B2 * | 11/2013 | Bentwich ............... A61N 2/006 600/12 |
| 8,626,259 B2 | 1/2014 | Besio |
| 8,706,181 B2 | 4/2014 | Stypulkowski et al. |
| 8,795,174 B2 | 8/2014 | Manicka et al. |
| 8,818,515 B2 | 8/2014 | Bikson et al. |
| 8,838,247 B2 | 9/2014 | Hagedorn et al. |
| 8,874,220 B2 | 10/2014 | Draghici et al. |
| 8,874,227 B2 | 10/2014 | Simon et al. |
| 8,880,173 B2 | 11/2014 | Diubaldi et al. |
| 8,903,494 B2 | 12/2014 | Goldwasser et al. |
| 8,938,301 B2 | 1/2015 | Hagedorn |
| 8,979,837 B2 | 3/2015 | De La Rama et al. |
| 8,989,863 B2 | 3/2015 | Osorio |
| 9,002,458 B2 | 4/2015 | Pal et al. |
| 9,080,918 B2 | 7/2015 | Fishel et al. |
| 9,186,505 B2 | 11/2015 | Katsnelson |
| 9,393,430 B2 | 7/2016 | Demers et al. |
| 9,399,126 B2 | 7/2016 | Pal et al. |
| 9,433,774 B2 | 9/2016 | Dar et al. |
| 9,440,063 B2 | 9/2016 | Ho et al. |
| 9,440,070 B2 | 9/2016 | Goldwasser et al. |
| 9,486,618 B2 | 11/2016 | Wingeier et al. |
| 9,517,345 B2 | 12/2016 | Meffin et al. |
| 9,630,005 B2 | 4/2017 | Wingeier et al. |
| 9,643,001 B2 | 5/2017 | Wu et al. |
| 9,731,127 B2 | 8/2017 | Kealey et al. |
| 9,757,561 B2 | 9/2017 | Wingeier et al. |
| 9,770,204 B2 | 9/2017 | Wu et al. |
| 9,782,585 B2 | 10/2017 | Wingeier |
| 9,802,042 B2 | 10/2017 | Wingeier et al. |
| 9,877,664 B2 | 1/2018 | MacHon et al. |
| 9,889,290 B2 | 2/2018 | Wingeier et al. |
| 9,913,973 B2 | 3/2018 | Yanaki |
| 9,981,128 B2 | 5/2018 | Wingeier |
| 10,238,870 B2 * | 3/2019 | Pilly ..................... A61B 5/486 |
| 10,293,162 B2 | 5/2019 | Wingeier |
| 2002/0169485 A1 | 11/2002 | Pless et al. |
| 2004/0019370 A1 | 1/2004 | Gliner et al. |
| 2005/0165460 A1 | 7/2005 | Erfan |
| 2006/0111754 A1 | 5/2006 | Ansarinia et al. |
| 2006/0212093 A1 | 9/2006 | Pless et al. |
| 2006/0229502 A1 | 10/2006 | Pollock et al. |
| 2006/0259094 A1 | 11/2006 | Grinshpoon et al. |
| 2007/0015984 A1 | 1/2007 | Yeo et al. |
| 2007/0023779 A1 | 2/2007 | Hirose et al. |
| 2007/0038265 A1 | 2/2007 | Tcheng et al. |
| 2007/0093706 A1 | 4/2007 | Gevins et al. |
| 2007/0118070 A1 | 5/2007 | Cormier et al. |
| 2007/0213783 A1 | 9/2007 | Pless |
| 2007/0237678 A1 | 10/2007 | Roesicke et al. |
| 2007/0237797 A1 | 10/2007 | Peyman |
| 2007/0238945 A1 | 10/2007 | Delic et al. |
| 2007/0250145 A1 | 10/2007 | Kraus et al. |
| 2008/0004676 A1 | 1/2008 | Osypka et al. |
| 2008/0021520 A1 | 1/2008 | Dietrich |
| 2008/0027345 A1 | 1/2008 | Kumada et al. |
| 2009/0069803 A1 | 3/2009 | Starkebaum |
| 2009/0099627 A1 | 4/2009 | Molnar et al. |
| 2009/0105785 A1 | 4/2009 | Wei et al. |
| 2009/0187159 A1 | 7/2009 | Greger et al. |
| 2010/0030129 A1 | 2/2010 | Nitzan et al. |
| 2010/0213070 A1 | 8/2010 | Oki et al. |
| 2010/0268287 A1 | 10/2010 | Celnik |
| 2010/0330589 A1 | 12/2010 | Bahrami et al. |
| 2011/0040291 A1 | 2/2011 | Weissenrieder-Norlin et al. |
| 2011/0054288 A1 | 3/2011 | Besio |
| 2011/0112590 A1 | 5/2011 | Molnar et al. |
| 2011/0118806 A1 | 5/2011 | Pascual-Leone et al. |
| 2011/0276112 A1 | 11/2011 | Simon et al. |
| 2011/0288610 A1 | 11/2011 | Brocke |
| 2011/0319975 A1 | 12/2011 | Ho et al. |
| 2012/0007832 A1 | 1/2012 | Lee et al. |
| 2012/0065699 A1 | 3/2012 | Bedenbaugh |
| 2012/0071947 A1 | 3/2012 | Gupta et al. |
| 2012/0078323 A1 | 3/2012 | Osorio |
| 2012/0184894 A1 | 7/2012 | Imran et al. |
| 2012/0191157 A1 | 7/2012 | Stypulkowski et al. |
| 2012/0226127 A1 | 9/2012 | Asjes et al. |
| 2012/0271377 A1 | 10/2012 | Hagedorn et al. |
| 2012/0289869 A1 | 11/2012 | Tyler |
| 2013/0085347 A1 | 4/2013 | Manicka et al. |
| 2013/0113059 A1 | 5/2013 | Song et al. |
| 2013/0184779 A1 | 7/2013 | Bikson et al. |
| 2013/0204315 A1 | 8/2013 | Wongsarnpigoon et al. |
| 2013/0261706 A1 | 10/2013 | Mirro et al. |
| 2013/0281759 A1 | 10/2013 | Hagedorn et al. |

(56) References Cited

U.S. PATENT DOCUMENTS

| | | |
|---|---|---|
| 2014/0069212 A1 | 3/2014 | Fishel et al. |
| 2014/0148872 A1 | 5/2014 | Goldwasser et al. |
| 2014/0172041 A1 | 6/2014 | Draghici et al. |
| 2014/0277324 A1 | 9/2014 | Diubaldi et al. |
| 2014/0316505 A1 | 10/2014 | Yanaki |
| 2014/0350431 A1 | 11/2014 | Hagedorn |
| 2015/0005841 A1 | 1/2015 | Pal et al. |
| 2015/0065838 A1 | 3/2015 | Wingeier et al. |
| 2015/0066104 A1 | 3/2015 | Wingeier et al. |
| 2015/0088224 A1 | 3/2015 | Goldwasser et al. |
| 2015/0238759 A1 | 8/2015 | Katsnelson |
| 2015/0238762 A1 | 8/2015 | Pal et al. |
| 2015/0328467 A1 | 11/2015 | Demers et al. |
| 2015/0335877 A1 | 11/2015 | Jeffery et al. |
| 2015/0352357 A1 | 12/2015 | Wei et al. |
| 2015/0352364 A1 | 12/2015 | Meffin et al. |
| 2015/0360027 A1 | 12/2015 | Bachinski et al. |
| 2015/0374971 A1 | 12/2015 | Dar et al. |
| 2015/0375007 A1 | 12/2015 | Takeuchi et al. |
| 2016/0017558 A1 | 1/2016 | French |
| 2016/0022981 A1 | 1/2016 | Wingeier et al. |
| 2016/0175589 A1 | 6/2016 | Wingeier |
| 2016/0184585 A1 | 6/2016 | Kealey et al. |
| 2016/0256105 A1* | 9/2016 | Boyle .................. A61N 1/20 |
| 2016/0303362 A1 | 10/2016 | Wu et al. |
| 2016/0346530 A1 | 12/2016 | Jeffery et al. |
| 2016/0360990 A1 | 12/2016 | Altshuler et al. |
| 2016/0361541 A1 | 12/2016 | Wingeier et al. |
| 2016/0366507 A1 | 12/2016 | Hou et al. |
| 2017/0021158 A1 | 1/2017 | Wingeier et al. |
| 2017/0224978 A1 | 8/2017 | Lee |
| 2017/0224990 A1 | 8/2017 | Goldwasser et al. |
| 2017/0361096 A1 | 12/2017 | Wingeier |
| 2017/0368344 A1 | 12/2017 | Ironi et al. |
| 2018/0021565 A1 | 1/2018 | Dar et al. |

FOREIGN PATENT DOCUMENTS

| | | |
|---|---|---|
| JP | 2010152731 A | 7/2010 |
| KR | 20150088224 A | 7/2015 |
| KR | 101685124 B1 | 12/2016 |
| KR | 20170021158 A | 2/2017 |
| KR | 20170028197 A | 3/2017 |
| KR | 20180021565 A | 3/2018 |
| WO | 2013113059 A | 3/1871 |
| WO | 2008048471 A2 | 4/2008 |
| WO | 2009134763 A1 | 11/2009 |
| WO | 2013004763 A1 | 1/2013 |

* cited by examiner

SYSTEM AMD METHOD FOR INDIVIDUALIZING NEUROMODULATION

CROSS-REFERENCE TO RELATED APPLICATIONS

This application is a continuation of U.S. patent application Ser. No. 16/195,728, filed Nov. 19, 2018, now issued as U.S. Pat. No. 10,507,324, which claims the benefit of U.S. Provisional Application No. 62/587,777, filed Nov. 17, 2017, which is incorporated in its entirety by this reference.

This application is related to U.S. application Ser. No. 15/250,070, filed Aug. 29, 2016, now issued as U.S. Pat. No. 10,434,301; U.S. application Ser. No. 16/168,607, filed Oct. 23, 2018, now issued as U.S. Pat. No. 10,596,373; U.S. application Ser. No. 15/426,212, filed Feb. 7, 2017, now issued as U.S. Pat. No. 10,315,033; U.S. application Ser. No. 15/962,233, filed Apr. 25, 2018, now issued as U.S. Pat. No. 10,293,162; and U.S. application Ser. No. 15/627,717, filed Jun. 20, 2017, now issued as U.S. Pat. No. 10,485,443; each of which is incorporated in its entirety by this reference.

TECHNICAL FIELD

This invention relates generally to the neuromodulation field, and more specifically to a new and useful system and method for individualizing neuromodulation in the neuromodulation field.

BACKGROUND

Modulation of neural activity of the brain through the application of stimulation has been shown to have numerous benefits in conjunction with the performance of tasks, such as improving user performance of the task, accelerating improvement in user performance of the task, achieving and retaining lasting learnings from the task, and enhancing user mood. While current neuromodulation devices can apply different types of stimulation patterns, these stimulation patterns are fixed among users and tasks, and do not optimize for these positive effects.

Thus, there is a need in the neuromodulation field to create a new and useful system and method for individualizing neuromodulation.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
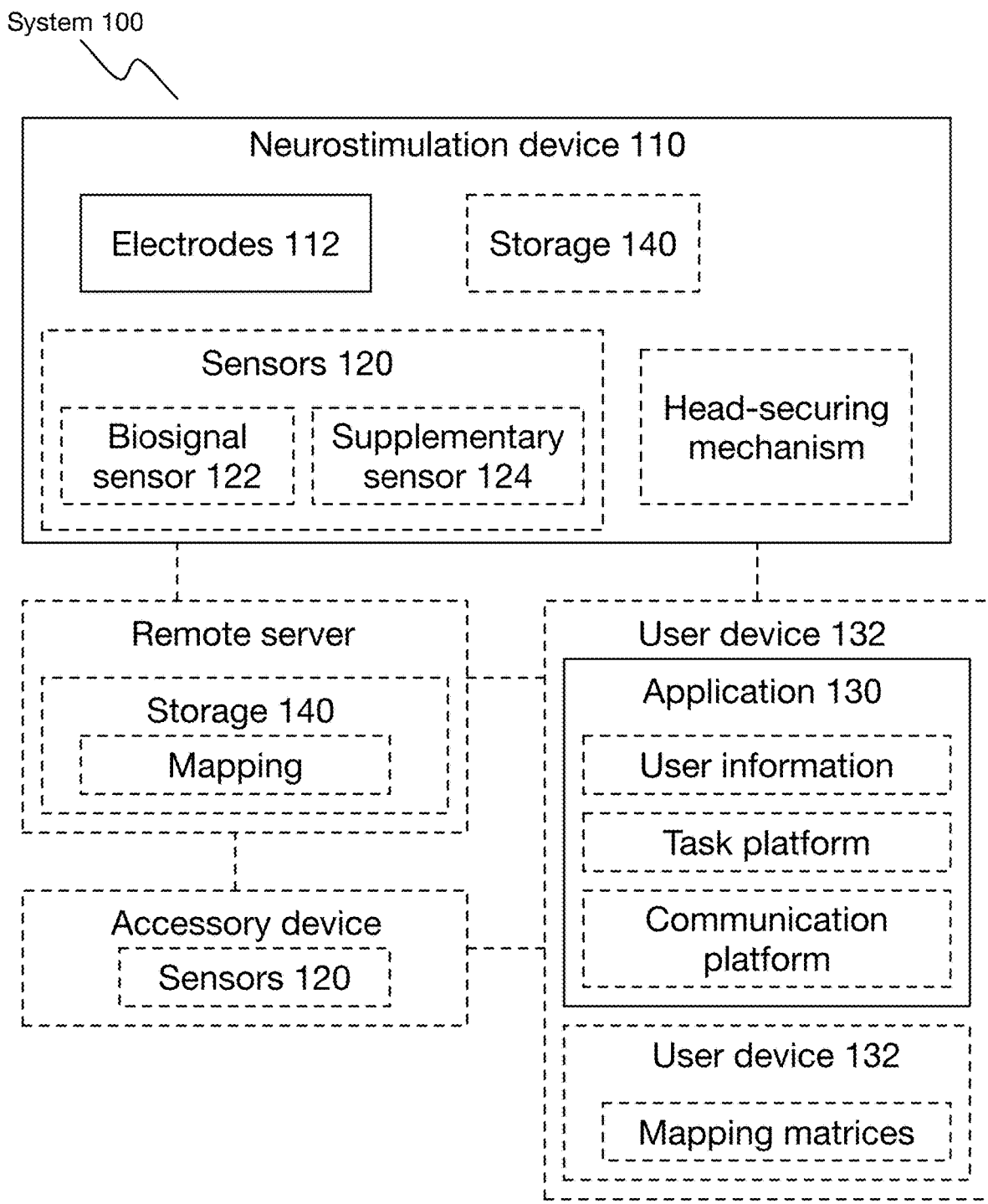
FIG. 1 is a schematic representation of the system for individualizing neuromodulation.

As shown in FIG. 1, a system 100 for individualizing neuromodulation includes a neurostimulation device 110 having a set of electrodes 112, and an application 130 executing on a user device 132. Additionally or alternatively, the system 100 can include any or all of: sensor system 120, a head-securing mechanism, a remote server, storage 140, an accessory device, and any other suitable component.

Figure 2:
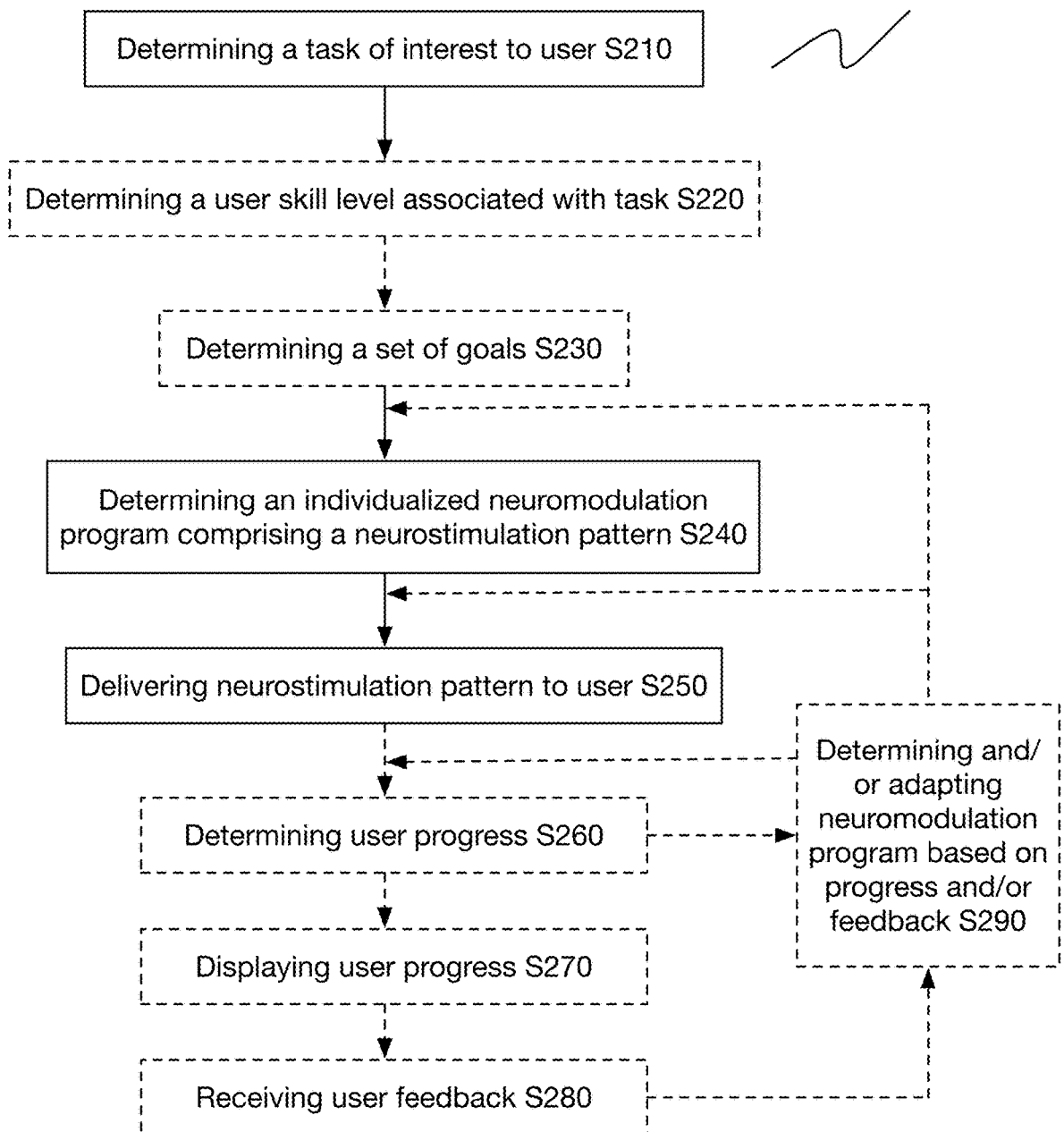
FIG. 2 is a schematic representation of the method for individualizing neuromodulation.

As shown in FIG. 2, a method 200 for individualizing neuromodulation includes determining a task of interest to a user S210 and/or determining a set of goals S230; determining an individualized neuromodulation program comprising a neurostimulation pattern S240; and delivering the neurostimulation pattern to the user. Additionally or alternatively, the method 200 can include any or all of: determining a user skill level associated with the task S220; determining user progress S260; displaying user progress S270; receiving user feedback S280; determining and/or adapting neuromodulation program based on user progress and/or user feedback S290; and any other suitable process.

2. Benefits.

The system 100 and method 200 can confer several benefits over current systems and methods for neuromodulation.

In some variations, for instance, the system and method confer the benefit of applying neurostimulation optimized for a particular task, wherein the optimization can function to: improve the user's performance of the task, decrease the time required for mastery of the task or improved performance of the task, optimize the order and/or timing in which a set of tasks or sub-tasks are performed, boost a user's mood or emotional state, cater the neurostimulation to a skill level of the user, and/or perform any other suitable function.

In some variations, the system and method confer the benefit of targeting a particular brain region, which can be enabled, for instance, through the selection of a particular subset of electrodes in a neurostimulation device through which to apply stimulation. This can function to apply neurostimulation to an optimal head region of a user (e.g., as guided by clinical or academic research, based on dynamic feedback from signals and/or data indicative of user performance on the task, and/or as guided by analysis of usage and/or human performance data collected from neurostimulation systems 100 in use by a population of users) as determined by the nature of the task. In a specific example, a first subset of electrodes is chosen to apply stimulation during a cognitive task (e.g., proximal to the forehead) whereas a second subset of electrodes (e.g., proximal to the motor cortex) is chosen to apply stimulation during an athletic task. In another specific example, a first current path through a subset of electrodes (e.g., a current path with cathode positioned over left dorsolateral prefrontal cortex) is chosen to apply stimulation during a phase of a cognitive task where increased creativity and/or less critical thinking is desired, such as ideation or brainstorming, and a second current path (e.g., a current path with anode positioned over left dorsolateral prefrontal cortex) is chosen to apply stimulation during a phase of a cognitive task where increased critical thinking is desired, such as critical analysis and filtering of ideas.

In some variations, the system and method confer the benefit of monitoring user progress and appropriately applying stimulation (e.g., stimulation type, duration, timing, frequency, schedule, etc.) based on this progress and the overall skill level of the user. In specific examples, the system and method confer the benefit of informing the user of his progress (e.g., through display on an application) and receiving user feedback with respect to the progress.

Additionally or alternatively, the system and method can confer any other suitable benefit(s).

3. System.

The system 100 functions to apply individualized neuromodulation to a user through the application of a set of one or more specific prescribed neurostimulation patterns through a set of electrodes. Additionally, the system 100 can include sensor system 120 with which to determine the state and/or progress of a user in relation to the applied neurostimulation. As such, the system 100 includes a neurostimulation device 110 having a set of electrodes 112, the neurostimulation device 110 in communication with a client application 130 (e.g., control system) executing on a user device. Additionally, the system can include any of the components described below and/or any other suitable component.

The system 100 includes a neurostimulation device 110, which functions to stimulate and/or modulate one or more brain regions of a user according to a prescribed stimulation pattern. The neurostimulation device preferably applies electrical stimulation (e.g., transcranial stimulation, transcranial direct current stimulation, transcranial alternating current stimulation, transcranial random noise stimulation, transcranial pulsatile stimulation, etc.) but can additionally or alternatively provide any other suitable form of stimulation (e.g., transcranial magnetic stimulation) or any combination of these forms of stimulation.

The stimulation is applied through a set of electrodes 112 (e.g., electrode pads, patches, electrode protrusions, etc.), which can include a compliant material such as a foam (e.g., polyvinyl alcohol; polyolefin; polyolefin with surfactant; cellulose; etc.), gel, sponge, or fabric; a conductive material (e.g., conductive polymer, conductive rubber, etc.); a rigid material; or any other suitable material(s). The system 100 can also include transducers such as ultrasound emitters, magnetic emitters, optical emitters, radio-frequency or low-frequency electromagnetic coils capable of signaling to implanted devices, or other transducers capable of inducing neuromodulation in addition to or alternatively to the set of electrodes 112. Throughout this description, any reference to "electrode" can be equally applied to the components described above and below (e.g., optodes, magnetic emitters, ultrasound emitters, electromagnetic emitters, coils capable of signaling to implanted devices, or other transducers capable of inducing neuromodulation). The set of electrodes 112 may be configured as individual electrodes, one or more sub-assemblies incorporating one or more individual electrodes of the set of electrodes 112, or any combination thereof.

The neurostimulation device 110 can include multiple electrodes 112 covering a variety of brain regions of the user. This can function, for instance, to enable the targeting of a specific brain region based on the selective application of stimulation through a particular subset of electrodes. Alternatively, the neurostimulation device 110 can be brain region and/or application specific; in a specific example, a set of electrodes of a first neurostimulation device covers one specific brain region (e.g., motor cortex) and/or is used in the context of a particular set of activities (e.g., athletic activities), whereas a second neurostimulation device 110 is used for a separate set of activities (e.g., cognition, mindfulness, focus, and/or attention-related activities).

Figure 5:
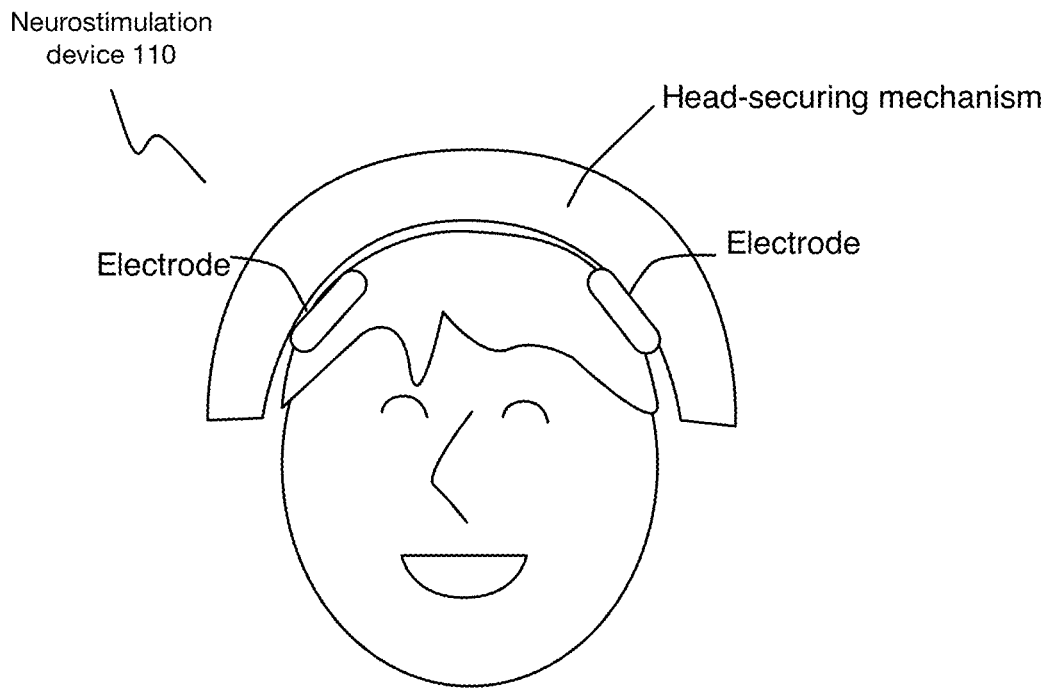
FIGS. 5-7 each represent a variation of the neurostimulation device.
Figure 6:
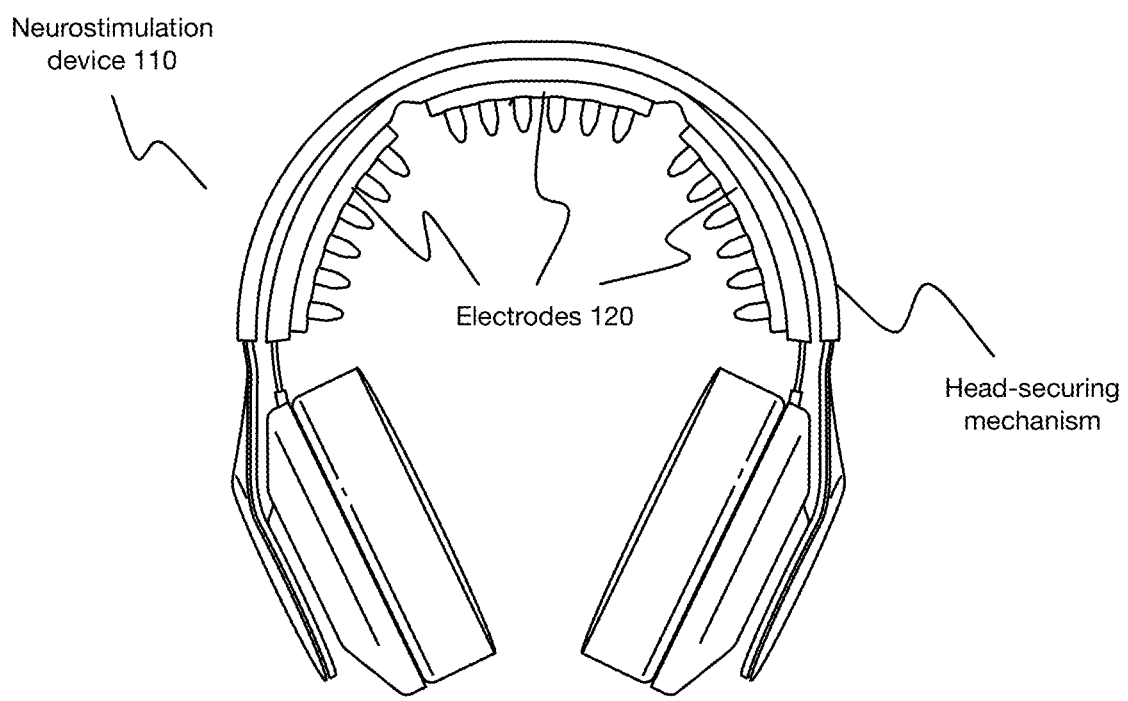
Figure 7:
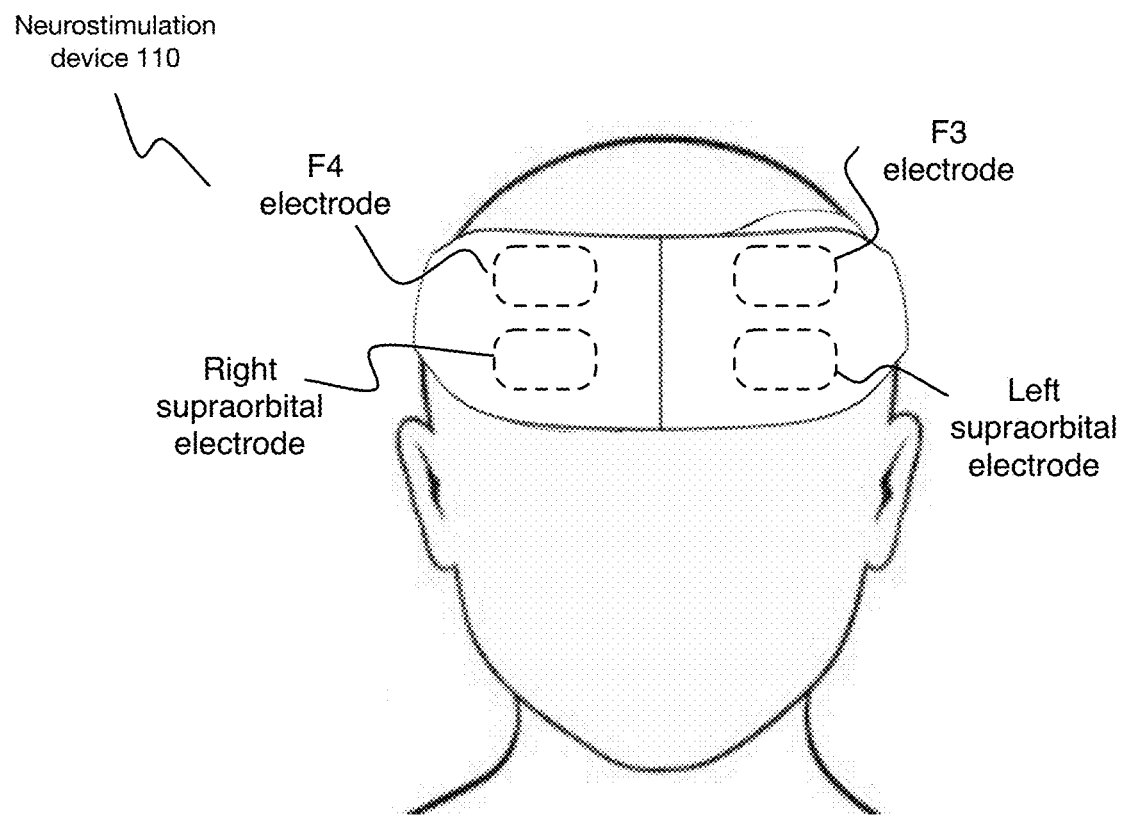

The neurostimulation device 110 can include or be configured to interface with a head-securing mechanism configured to be applied to a head region of the user. The head-securing mechanism can include any suitable components, such as: fasteners (e.g., straps, bands, etc.), support features, cushioning, hats, or other suitable materials to secure the neurostimulation device to the head of a user. In one variation, the neurostimulation device 110 includes a headband (e.g., as shown in FIG. 5, as shown in FIG. 6) to secure a set of electrodes proximal to a motor cortex brain region of the user. In another variation (e.g., as shown in FIG. 7), the neurostimulation device 110 includes a strap configured to be worn around the back of the head and/or neck of the user, such that a set of electrodes are secured to the forehead of the user.

In some variations, the neurostimulation device 110 includes any or all of the systems described in U.S. application Ser. No. 15/335,240, filed 26 Oct. 2016, U.S. application Ser. No. 15/916,170, filed 8 Mar. 2018, and U.S. application Ser. No. 15/916,179, filed 8 Mar. 2018, each of which is incorporated herein in its entirety by this reference. In some variations, this neurostimulation device 110 can be used to implement the systems and/or methods disclosed in U.S. application Ser. No. 15/962,233 filed 25 Apr. 2018, incorporated herein in its entirety by this reference. Additionally or alternatively, the neurostimulation device 110 can include any other suitable system and/or be used in any other suitable manner.

The system 100 can additionally include one or more sensor systems 120 which function to assess a state of the user and/or the progress of a user in the performance of a task. Assessing a user state can be performed while stimulation is being applied, in response to stimulation being applied (e.g., after a session of neurostimulation, such as a session of neurostimulation intended to prepare the brain for optimal performance or learning during a subsequent task), prior to stimulation being applied (e.g., to serve as a baseline state), independent of stimulation being applied (e.g., during a particular task, during a resting state, etc.), continuously, intermittently, or at any other time.

The sensor system 120 can include one or more sensors 122, more preferably biosignal sensors (e.g., configured to measure electrocardiogram (ECG) signals, voluntary muscle contraction, maximum voluntary muscle contraction, galvanic response, evoked potential, electromyography (EMG) signals, electroencephalography (EEG) signals, neuroimaging sensors such as a functional near-infrared spectroscopy (fNIRS) system, etc.), but alternatively any suitable set of sensors, which function to assess a physiological state of the user. Additionally or alternatively, the sensor system 120 can include one or more supplementary sensors 124, which can function to measure a performance of a user (e.g., athletic performance). The supplementary sensors 124 can include any or all of: motion sensors (e.g., accelerometer, gyroscope, etc.), position sensors, optical sensors (e.g., camera, eye tracking system, etc.), inertial sensors, force sensors, strain sensors, or any other suitable sensors.

The sensor system 120 can be part of any or all of: the neurostimulation device (e.g., ECG sensors integrated into device), an accessory component or other device separate from the neurostimulation device 110, such as an accessory associated with a task performed in the method (e.g., gaming equipment such as a controller, joystick, computer, television, etc.; sporting equipment: sensors (e.g., accelerometer) of sporting equipment such as tennis racket, golf club, ball, etc.; sensors integrated into a user device etc.).

The system 100 can additionally include an application 130 (e.g., client application) executing on a user device 132, wherein the application is communicatively connected (e.g., wirelessly connected) to the neurostimulation device 110. In some variations, the application 130 is configured to control the delivery of the neurostimulation pattern. Additionally or alternatively, the application 130 is configured to receive user feedback, provide (e.g. administer, present, etc.) the task (e.g., game) for which neurostimulation is contemporaneously delivered, track and/or display user progress (e.g., as shown in FIG. 9C), record auxiliary sensor signals (e.g., of sensors attached to user tools indicative of user progress, such as a golf club), or perform any other suitable function.

Figure 11:
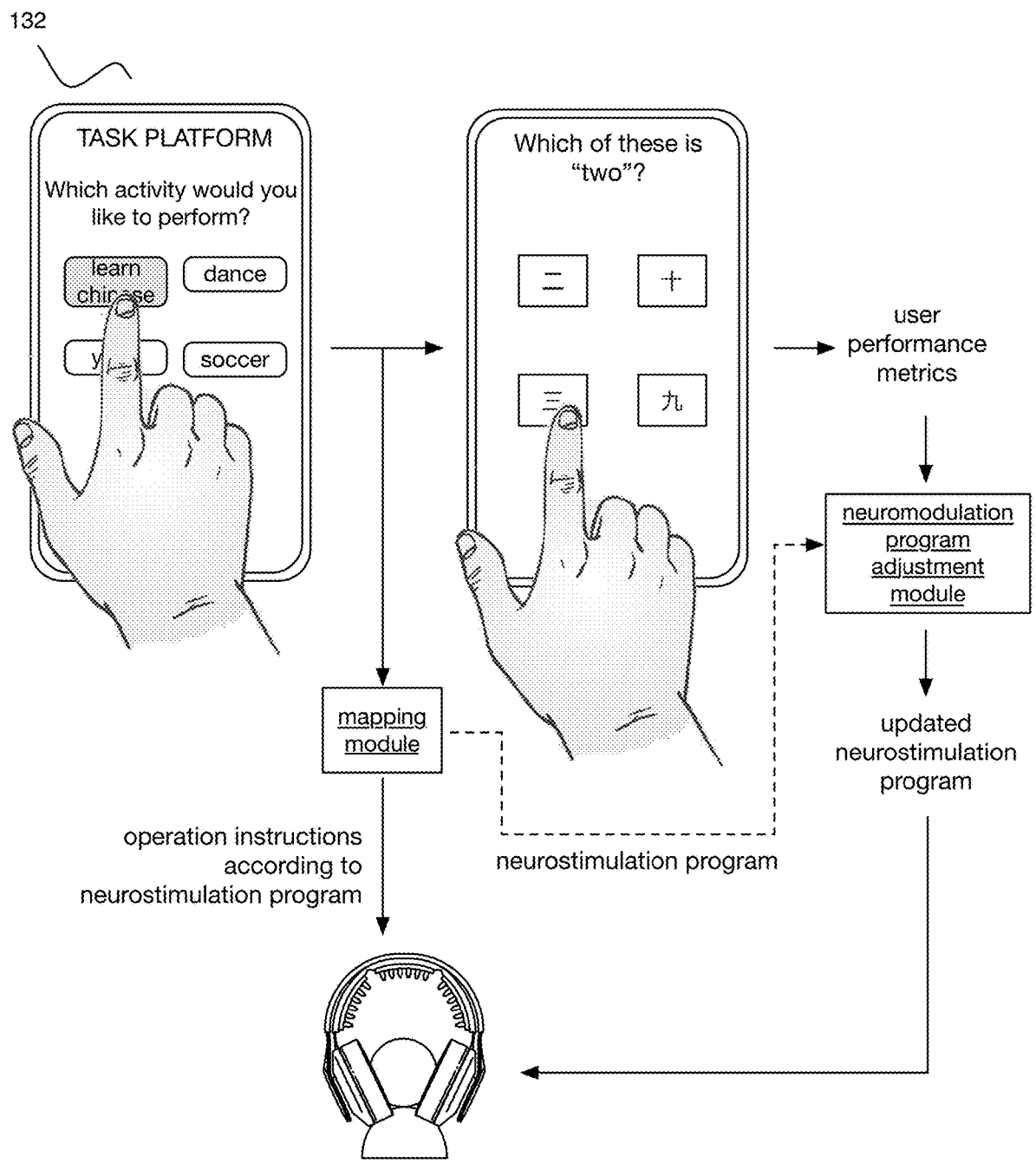
FIG. 11 is a schematic representation of a specific example of neurostimulation program updating based on user performance.

The application 130 can additionally be in communication with one or more sensors of the sensor system 120, wherein the application receives data taken from the sensors. Further additionally or alternatively, the application 130 can be in communication with a remote server and or remote storage. In some variations, for instance, part or all of the processing involved in the determination and creation of neurostimulation patterns is done at a remote server, wherein the application can query the remote server (e.g., to send a neurostimulation pattern) and/or the remote server can query the application (e.g., to send a software update, to receive a user state or performance data, etc.). Additionally or alternatively, the sensor system 120 and/or supplementary sensors 124 can include human-input devices such as a mouse, keyboard, or touch screen, for instance human-input devices integrated into a user device 132 and managed by the application 130, for instance in an application intended to improve performance of the user on a cognitive task which is presented to the user on the user device. In one example, the application 130 presents all or a portion of the game or task to the user (e.g., presents a chess game to the user; presents a foreign language learning program to the user; presents a standardized test preparation curriculum to the user; etc.), concurrently monitors user performance during user interaction with the game or task (e.g., scores the user based on performance metrics associated with the game, task, or neuromodulation goals; etc.), and can optionally dynamically adjust the neurostimulation program (e.g., the neurostimulation pattern) applied to the user (e.g., using a neuromodulation program adjustment module; specific example shown in FIG. 11). In another example, a second application executing on a secondary device (e.g., a smart chess board, connected or smart athletic equipment, etc.) can dynamically monitor user performance and stream the raw signals and/or derivative data (e.g., summary data, trends, etc.) to the primary application 130 for analysis and use; and/or perform any of the tasks discussed above. However, the application 130 can perform any other suitable functionality.

The application 130 can include user information, such as, but not limited to, personal identifiers, demographic information, user preferences, interests, history, or any other information. The user information can be entered by the user, determined through the user's online presence (e.g., social media, information gathered through internet searches, etc.), determined from the user's medical history, or otherwise determined.

Figure 9A:
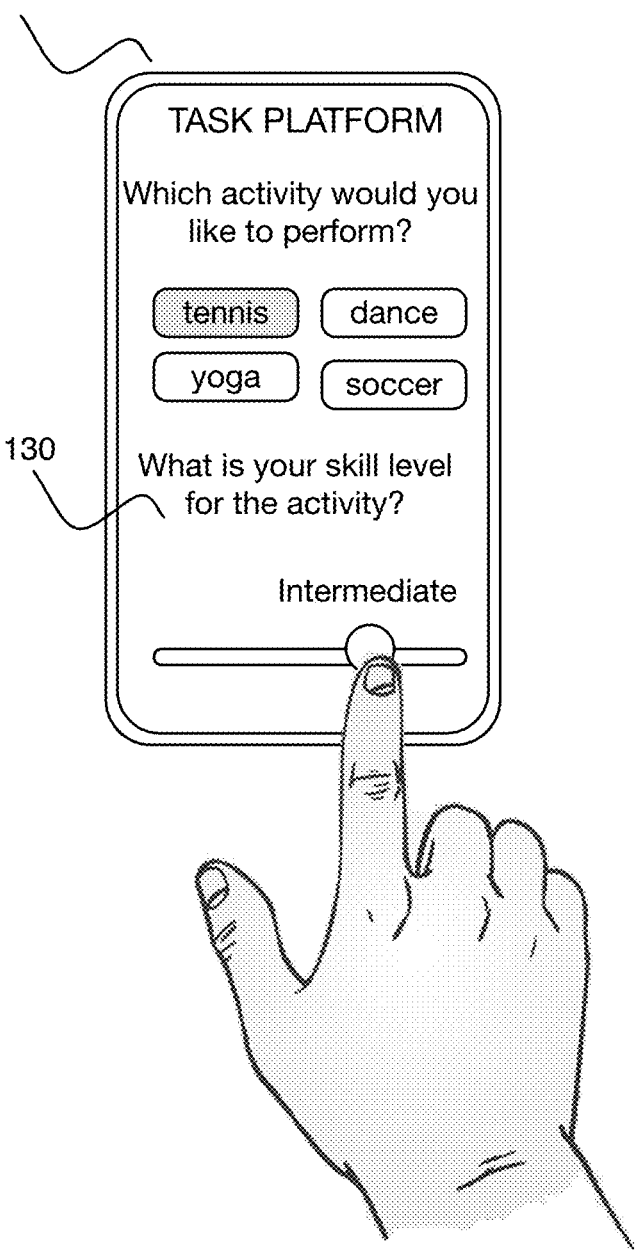
FIGS. 9A-9C represent a variation of the method involving a tennis task.

The application 130 can additionally include a task platform (e.g., as shown in FIG. 9A), which functions to provide an interface for one or more activities (tasks) for the user to perform. This can include, for instance, games or other exercises (e.g., mindfulness exercises and/or cognitive games) to test user performance and/or assess user state (e.g., aptitude, concentration, focus, memory, recall, critical thinking, relaxation, stress, emotional response, etc.).

Additionally or alternatively, the application 130 can collect performance and user state metrics in temporal relation (e.g., during, after, prior, etc.) with a task. These metrics can include any or all of: user feedback, user scores during task, answers to questions presented to the user (e.g., throughout the task, as a follow-up questionnaire after a task, as a pre-survey before a task, etc.), collected data (e.g., sensor data), or any other suitable metric.

In some variations, the application 130 includes a communication platform configured to facilitate communication between different users, between a user and a coach (e.g., task-specific coach), or between any other individuals.

The application preferably executes on a user device 132, such as a mobile phone (e.g., cell phone), tablet, computer (e.g., laptop computer, desktop computer, etc.), but can additionally or alternatively be executed on any suitable device or set of devices.

The system 100 can include storage 140, which can function to store any or all of: matrices (e.g., mapping matrices) as described below, databases (e.g., storing the mapping algorithms, matrices, etc.), stimulation patterns, user information, user performance/progress data (e.g., task performance history, scores, etc.), or any other suitable information. The storage 140 can be in the form of client-side storage (e.g., storage in user device 132), server-side storage (e.g., cloud-based storage, local storage, etc.), storage onboard neurostimulation device, or any other storage in any suitable location(s). In some variations, the storage 140 is split or distributed among multiple locations (e.g., devices). In a specific example, for instance, user progress is stored in client-side storage whereas neurostimulation patterns are stored in cloud-based storage and transmitted to the application prior to delivery at the neurostimulation device 110.

Additionally, the system 100 can include any other suitable component(s).

4. Method.

The method 200 functions to optimize the user experience and the magnitude of positive effects achieved by neurostimulation through the application of individualized neuromodulation. The method 200 is preferably performed with a system as described above but can additionally or alternatively be performed with any suitable system. As shown in FIG. 2, the method 200 for individualizing neuromodulation includes determining a task of interest to a user S210; determining a set of goals S230; determining an individualized neuromodulation program comprising a neurostimulation pattern S240; and delivering the neurostimulation pattern to the user. Additionally or alternatively, the method 200 can include any or all of: determining a user skill level associated with the task S220; determining user progress S260; displaying user progress S270; receiving user feedback S280; determining and/or adapting neuromodulation program based on user progress and/or user feedback S290; and any other suitable process.

4.1 Method—Determining Task of Interest to User S210

Determining a task of interest to the user S210 functions to produce an input with which an individualized neurostimulation pattern is determined. Additionally or alternatively, determining a task of interest can function to select a predetermined neurostimulation pattern, serve as a label assigned to a dataset recorded during the performance of a task, or perform any other suitable function.

The task of interest can be determined through any or all of: selection by a user (e.g., at an application 130); the application of a set of models or algorithms (e.g., based on user information such as general user interests; a deep learning model; with a predictive algorithm; etc.); a predetermined or preset selection or listing of tasks (e.g., sequential listing); a user questionnaire; a user history (e.g., most recently performed task, most frequently performed tasks, etc.); aggregated data (e.g., overall user trends, most popular tasks, etc.); environmental information; or any other suitable factor.

In some variations, the task of interest is determined based on a user onboarding process (e.g., upon first setting up the neurostimulation device 110) through which the user's interests, skills, and/or goals are determined through a series of questions and then stored. In a specific example, a survey presented at an application 130 identifies particular areas of weakness and areas of desired focus for the user, such as leg endurance, dexterity, focus under stress, or any other suitable focus area.

The task of interest can include any or all of: a physical task (e.g., athletic training, athletic performance or sporting event, playing an instrument, etc.); a mental task (e.g., game; mental training activity for concentration, focus, energy, calm, etc.; cognitive exercise such as practice for a standardized test; language learning; etc.); a routine or unplanned activity of the user in his or her daily life (e.g., as determined through a sensor of the neurostimulation system 100; as determined by the sensor system 120, etc.); or any other suitable task or activity.

In some variations, an application 130 at a mobile device queries the user about his interests, the user makes a selection, and the task of interest is determined based on the selection.

4.2 Method—Determining a User Skill Level Associated with the Task of Interest S220

Figure 3:
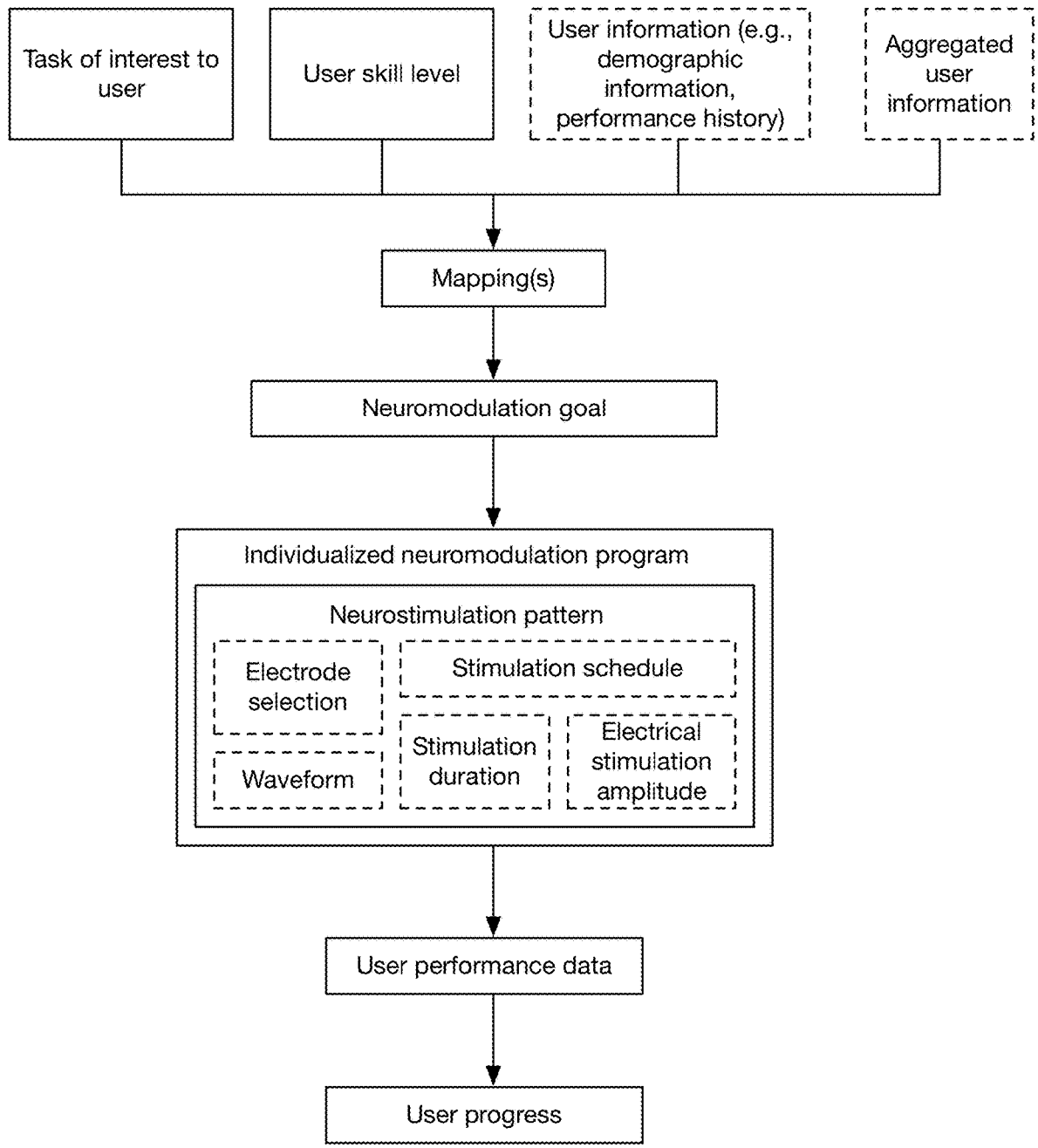
FIG. 3 is a schematic representation of a variation of the progression of outputs determined during the method for individualizing neuromodulation.

The method can optionally include determining a user skill level associated with the task of interest S220 functions to further inform the determination of an individualized neurostimulation pattern (e.g., as shown in FIG. 3). The user skill level can be specific to the particular user, aggregated from data of multiple users (e.g., users having performed the same type and/or number of tasks of interest as the user), predicted using a model or algorithm, or otherwise determined. The user skill level can include any or all of: an overall skill level associated with the task of interest, a skill level associated with a sub-task or focus area of the task of interest (e.g., overhand serve sub-task of a volleyball task of interest), a general skill level (e.g., unassociated with the task of interest), or any other suitable skill level type.

Figure 12:
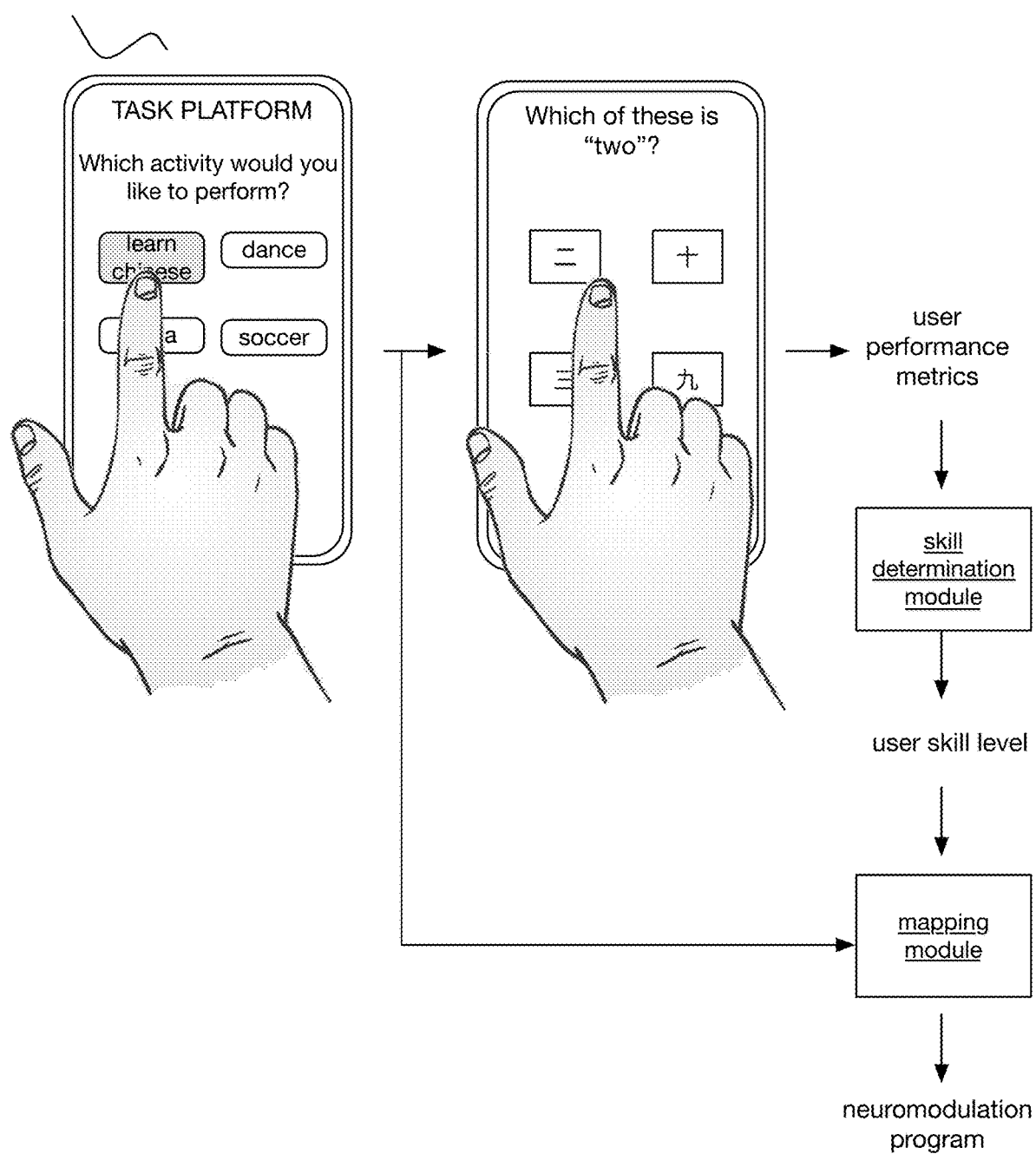
FIG. 12 is a schematic representation of a specific example of determining a user's skill level.

The user skill level can be selected by the user (e.g., at an application 130, at a web browser, etc.), determined based on previous data collected from the user or a device associated with the user (e.g., performance data, sensor data, progress info, stimulation history, etc.; specific example shown in FIG. 12), aggregated data (e.g., from a variety of users, from a group of users who performed said task, from a group of users who share the same skill level), determined based on external sensor data (e.g., attached to a user tool, wherein skill analysis algorithms, such as neural networks, heuristics, or pattern matching algorithms, can be applied to the external sensor data to classify the user skill level), predetermined, fixed, predicted, or otherwise determined. The user skill level can be determined (e.g., using a skill determination module) using: classification, heuristics, probabilities, one or more neural networks, a decisionmaking tree, patternmatching, a rule set, or otherwise determined.

S220 is preferably performed in response to S210 and at the same interface (e.g., application 130), but can additionally or alternatively be performed in prior to S210, in place of S210, in absence of S210, at a different interface (e.g., S210 performed at remote server, S220 received at application 130), or otherwise performed. Additionally or alternatively, determination of the user skill level S220 can include assigning a default, basic, and/or initial skill level to the user (e.g., from user input; from an initial test and automatic user skill classification or determination, such as benchmarking; from preknowledge of typical skill levels in the user population; etc.).

In one variation, the user declares his skill level at an application 130 contemporaneously with (e.g., during, after, etc.) the selection of the task of interest. Additionally or alternatively, the user skill level can be determined based on previous data (e.g., previous performance data, progress metric, stimulation history, etc.).

4.3 Method—Determining a Set of Goals S230

Determining a set of goals (e.g., neuromodulation goals) S230 can also function to inform the determination of an individualized neurostimulation pattern. Additionally or alternatively, the set of goals can function to establish a baseline against which to measure performance and/or progress. The set of goals preferably indicate a particular area of improvement (e.g., musculoskeletal control, visuomotor coordination, visual attention, vigilance, emotional control, memory, cognitive empathy, communication, concentration, focus, etc.) associated with (e.g., enabled by, enhanced by, etc.) performance of the task of interest, but can additionally or alternatively correspond to goals associated with multiple tasks of interest, be unassociated with the task of interest, be a desired outcome, or be otherwise determined. The set of goals can additionally or alternatively be mapped to an importance or weight for each of a given set of available areas for improvement. For example, an expert goal for chess can be associated with a high weight for vigilance, cognitive empathy, and memory, medium weight for visual attention, vigilance, and emotional control, and low weight for musculo-skeletal control and visuomotor coordination, while a novice goal for chess can be associated with a high weight for only cognitive empathy and memory, medium weight for visual attention, vigilance, and emotional control, and low weight for musculo-skeletal control and visuomotor coordination. However, the goals can be otherwise mapped.

The set of goals is preferably determined based on a set of inputs including the task of interest, the user skill level, and/or one or more mappings (e.g., as described below). Additionally or alternatively, the set of goals can be determined based on a subset of these factors, another factor, the application of one or more models (e.g., deep learning models, predictive algorithms, etc.), or otherwise determined. In some variations, determining a set of goals S230 can be combined with and/or merged with determining a task of interest to the user S210, or a default set of goals may be predetermined for a given task of interest. In still other variations, S230 can be excluded or performed at a later instance of the method.

Each of the mappings is preferably in the form of a matrix (e.g., decision tree, table, lookup table, etc.), wherein the matrix maps the series of inputs to one or more neuromodulation goals. Additionally or alternatively, the matrix or set of matrices can map the inputs directly to a neurostimulation pattern, an intermediate endpoint (e.g., first matrix which determines a subsequent matrix), or any other suitable output. In variations having multiple mappings (e.g., wherein a given set of input values maps to multiple neuromodulation goals), the mappings can be independent of each other, chained together, prioritized (e.g., globally prioritized; prioritized for the user based on user history or response, etc.), or otherwise related (e.g., nested). Multiple mappings can be executed in series, in parallel, or a combination of both. Additionally or alternatively, the input-to-goal mappings can be determined using: a rule set, predefined heuristics, a trained neural network, or otherwise determined.

The mappings can be fixed or dynamic (e.g., updated routinely, updated based on user progress, etc.); predetermined or determined in response to receiving a user skill level or interest; or otherwise determined. When the mappings are dynamic, the goals (e.g., neuromodulation operation parameters) can be iteratively adjusted (e.g., until user progress matches a target progression), adjusted according to a predetermined algorithm or rule, randomly adjusted, or otherwise adjusted. The mappings are preferably stored in a single location (e.g., remote computing system, client-side storage, local computing system, etc.), but can alternatively be distributed among multiple storage locations (e.g., first mapping stored on client-side storage which initiates a second mapping stored in cloud). In variations having one or more mappings stored remotely, the method 200 can further include initiating a query at an application 130 to retrieve the neuromodulation goal (or an intermediate output) from remote storage.

Figure 4A:
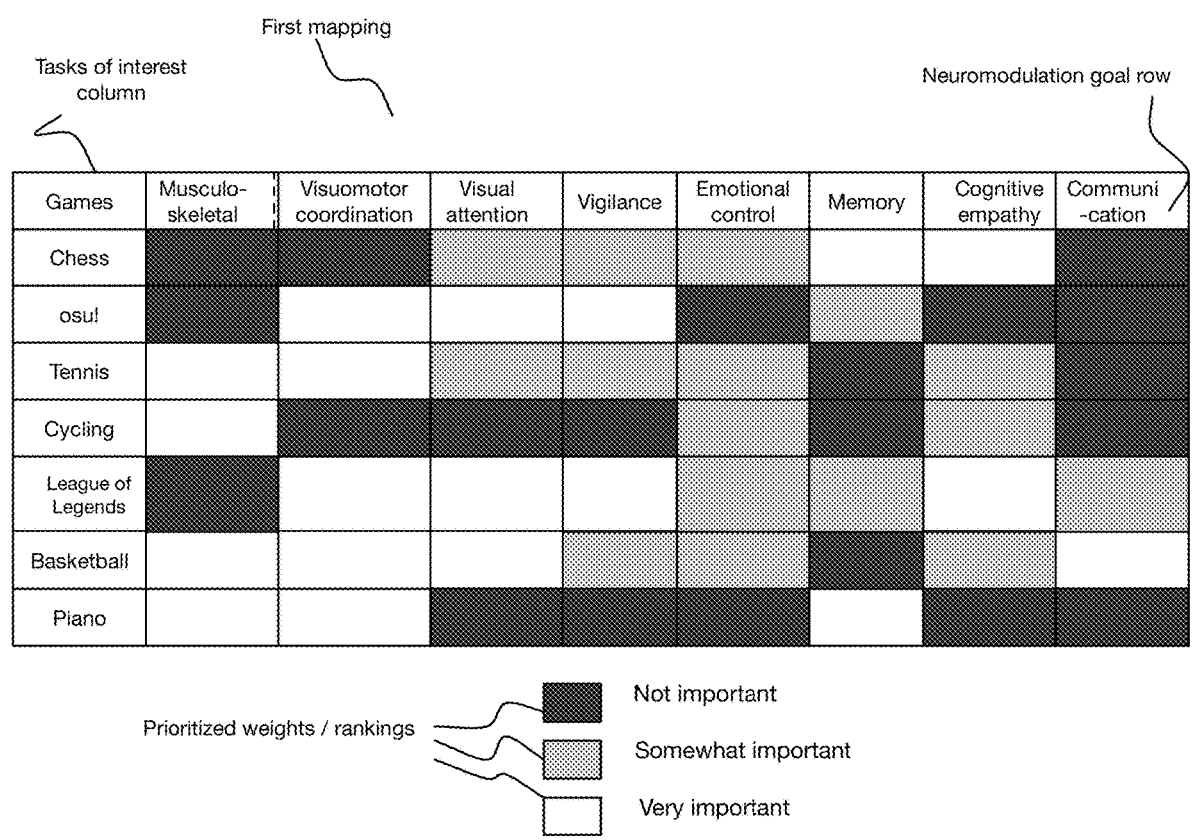
FIGS. 4A and 4B represent a variation of a set of mapping matrices.

In some variations (e.g., as shown in FIG. 4A), one or more mappings assigns a weight, ranking, or any other type of prioritization of one or more goals. Additionally, the mappings can prioritize the inputs (e.g., user skill level) used to determine the neuromodulation goal (e.g., prioritize user performance history over user self-selected skill level). In some variations, for instance, goals are temporally prioritized based on a predetermined ordered list. The goals can be prioritized based on any or all of: user preference, a desired user endpoint (e.g., user desire to master backhand swing within a predetermined time period), an assigned importance score, successful prioritizations for similar users (e.g., having a similar demographic, similar history, similar response rate, similar sensor outputs, similar skill level, etc.), or other suitable factor.

Figure 4B:
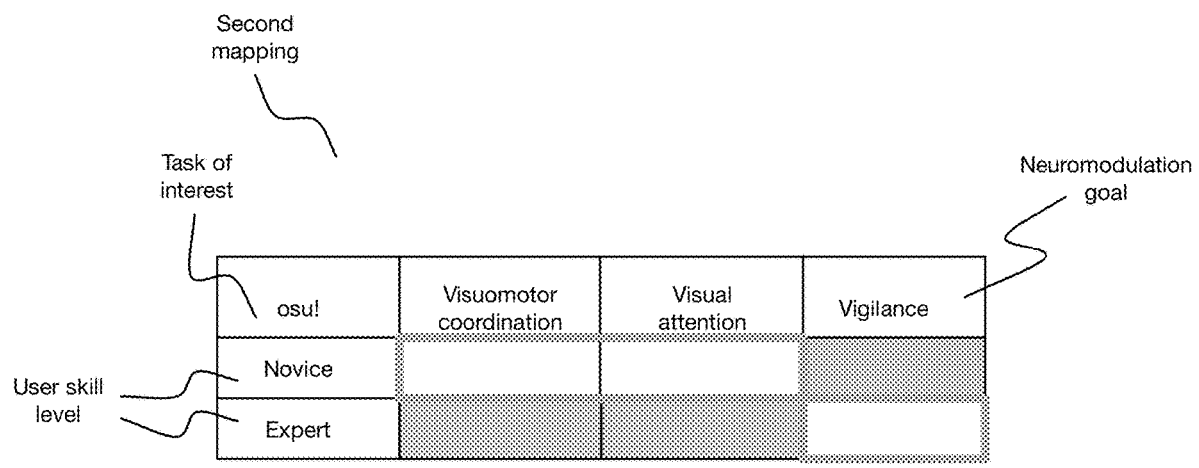

In one variation (e.g., as shown in FIGS. 4A and 4B), a first mapping matrix relates a set of potential tasks of interest to a set of potential neuromodulation goals associated with each task of interest, where the goals are prioritized (e.g., ranked, given a weighted score, etc.) based on their relevance and/or importance to the task of interest. These prioritized scores can be user-specific (e.g., determined based on performance history, preferences, skill level, etc.), user-agnostic, determined from aggregated user date, fixed, dynamic, or otherwise determined. A second mapping matrix then relates the set of goals to a set of potential user skill levels.

In some variations, an application 130 retrieves a set of prioritized neuromodulation goals appropriate to the task of interest and user skill level as received at the application, wherein the neuromodulation goals are retrieved from mapping matrix. In a first specific example, the neuromodulation goal includes a specific movement or targeted body region associated with a particular sport (e.g., golf, tennis, soccer, etc.). In a second specific example, the neuromodulation goal includes a memory goal (e.g., duration, volume, etc.) associated with a game or mental task (e.g., chess, retention of a set of flash card concepts, etc.). In a third specific example, the neuromodulation goal includes a desired duration of concentration in a particular environment (e.g., high stress environment, work environment, etc.).

4.4 Method—Determining an Individualized Neuromodulation Program Comprising a Neurostimulation Pattern S240

Determining an individualized neuromodulation program comprising a neurostimulation pattern S240 functions to prescribe a set of one or more neurostimulation patterns to a neurostimulation device 110 in an attempt to achieve the set of neuromodulation goals.

The neuromodulation program includes a set of one or more prescribed neurostimulation patterns, each of the neurostimulation patterns defined by any or all of: one or more electrical stimulation parameters (e.g., current amplitude, voltage amplitude, direct current stimulation parameter, alternating current stimulation parameter, waveform type, frequency, power, etc.), a duration of stimulation (e.g., 20 minutes, 1 hour, less than 20 minutes, greater than 20 minutes, etc.), a stimulation schedule (e.g., time at which to apply the neurostimulation pattern, frequency at which neurostimulation pattern is applied, recurrence of a neurostimulation pattern, ordering of a series of neurostimulation patterns, etc.), a neurostimulation device identifier, or any other suitable feature. Additionally, the neurostimulation pattern can prescribe an electrode montage (e.g., configuration with respect to location, polarity, and/or apportioning of electrical current, and/or subset of electrodes used) of stimulation, which can be implemented, for instance, through the selection of a subset of electrodes at which stimulation is applied. The electrode montage can include: the stimulation locations (e.g., electrode identifiers, electrode group identifiers, physiological locations, headset locations; subset of electrodes used; etc.), the stimulation polarity (e.g., cathodal or anodal; per electrode; relative to ground; relative to a return electrode; relative to the user; polarity over time; etc.), the stimulation patterns (e.g., which electrodes are stimulated at what time, the stimulation amplitude, the stimulation wavelength, the stimulation duration, etc.), the apportioning of electrical current (e.g., what fraction of the total electrical current is provided through each electrode or group of electrodes), and/or any other suitable stimulation features. In one example, the electrode montage can include one or more neurostimulation configurations specifying the electrodes to be stimulated at a given time in the neurostimulation pattern and the polarity at which the electrodes are to be stimulated. However, the montage can additionally or alternatively include operation instructions for any other suitable set of system outputs. The location and/or particular subset of electrodes can be determined through any or all of: known functional anatomy (e.g., known correlations between brain region and brain function), neuroimaging (e.g., fNIRS, magnetic resonance imaging (MRI), functional MRI, computed tomography, etc.), academic and/or clinical research, analysis of usage and/or performance data from the user or other users of the neurostimulation system 100, or any other suitable knowledge. In addition or alternative to the selection of a subset of electrodes, the method can include guiding a user to properly place the set or a subset of electrodes to a particular brain region.

The neuromodulation program can be determined based on a set of one or more mappings (e.g., mapping matrices, referencing a lookup table, reference a decision tree, algorithms, rule sets, neural network, etc.), such as the mappings described in S230 (e.g., same mapping used to determine the neuromodulation goal, separating mapping from that used to determine the neuromodulation goal, mapping which determines a single neurostimulation pattern based on a set of multiple goals, etc.) but alternatively a different set of mappings; directly assigned based on the neuromodulation goal; chosen by a user (e.g., selected from multiple neurostimulation pattern options such as multiple duration options); predetermined; or otherwise determined. Additionally or alternatively, the neuromodulation program can be determined based on any or all of: a user schedule, user anatomy, user health and health history, or any other suitable parameter(s).

Figure 10:
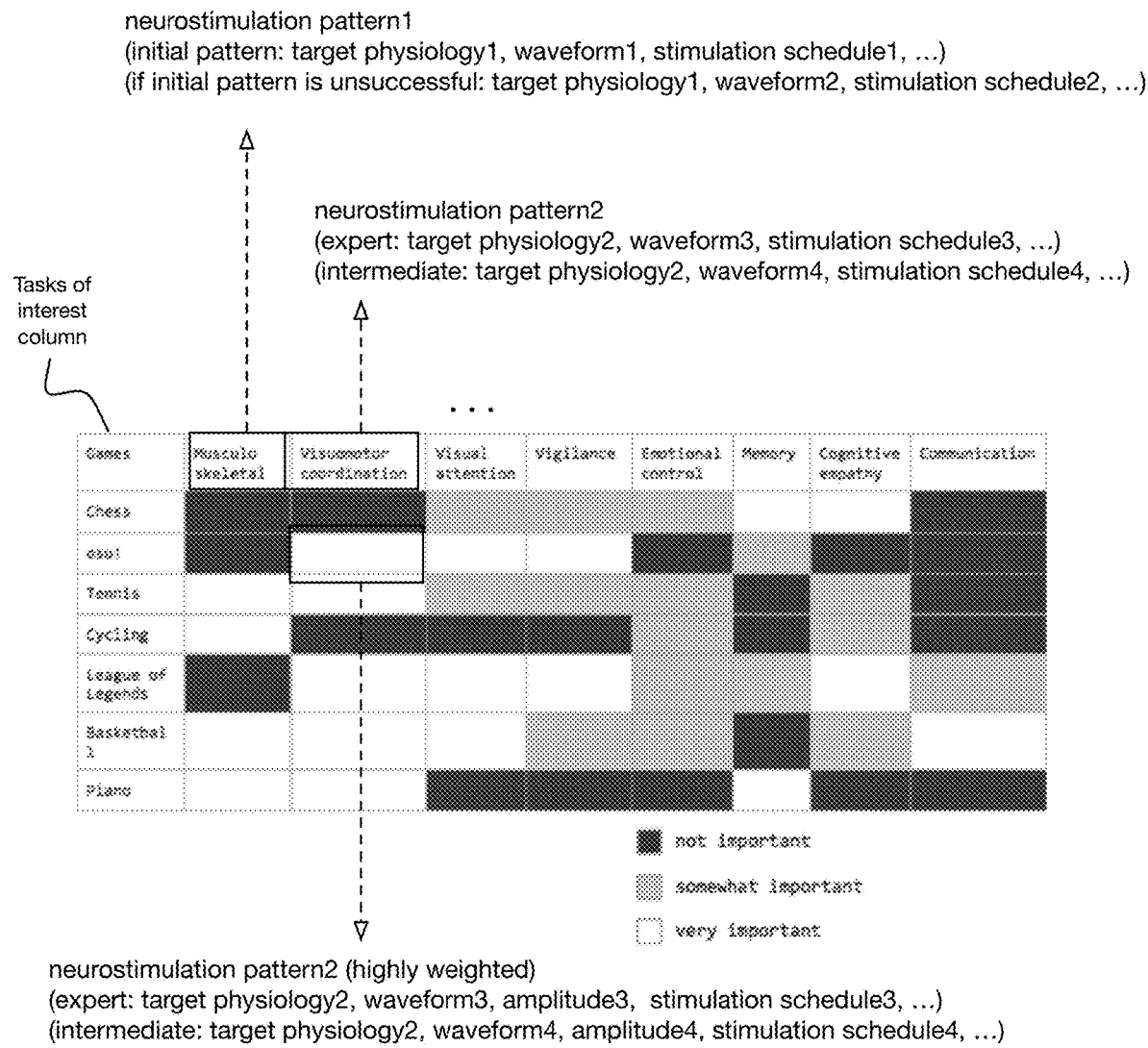
FIG. 10 is a schematic representation of a specific variation of goal mapping to different neurostimulation patterns.

As shown in FIG. 10, in one variation, each area of improvement is associated with a set of neuromodulation targets (e.g., target values, target physiological locations, associated electrodes, etc.), waveforms, stimulation schedules, and/or any other suitable set of neuromodulation operation parameter values or neurostimulation patterns. The goal selected in S230 can dictate the weight for each area of improvement, wherein the weight can: dictate whether the respective set of neuromodulation operation parameter values associated with the given area of improvement is included in the pattern; prioritize the respective neuromodulation operation parameter values; adjust (e.g., sum, average, etc.) the respective neuromodulation operation parameter values; dictate which neuromodulation operation parameter values are selected (e.g., wherein each area of improvement is associated with a set of operation parameter values); or otherwise influence how the neuromodulation operation parameter values associated with each area of improvement are included in the program. For example, a "chess" task can prioritize vigilance and emotional control, which is associated with a first and second set of neuromodulation operation parameter values (e.g., stimulating the prefrontal cortex). An "expert" goal for "chess" can dictate the stimulation patterns applied to the prefrontal cortex. However, the task and goal combinations can be otherwise used to determine the neuromodulation operation parameter values to be applied to the user. The neuromodulation operation parameter values associated with each area of improvement can be: manually defined, learned (e.g., from the neuromodulation data from a user population), calculated (e.g., based on user history, user progress, sensor output, etc.), recorded from an individual (e.g., a professional in the task; a user of the target skill level for the task; etc.), or otherwise determined.

In some variations, S240 includes determining and sending an alert to a user, the alert serving as an indicator or reminder for the user to receive the stimulation pattern(s) of the neuromodulation program. In a specific set of examples, an application 130 reminds the user to perform a neuromodulation session through the sending of a message (e.g., text, email, etc.) or the initiation of an alarm.

S240 is preferably performed in response to S230 but can additionally or alternatively be performed concurrently with S230, in absence of S230, multiple times throughout the method, or at any other time during the method. Further alternatively, the method can be performed in absence of S240. In some variations, for instance, the user can use the system for his own plan and goals (e.g., outside of a structured program in the application 130).

Figure 8:
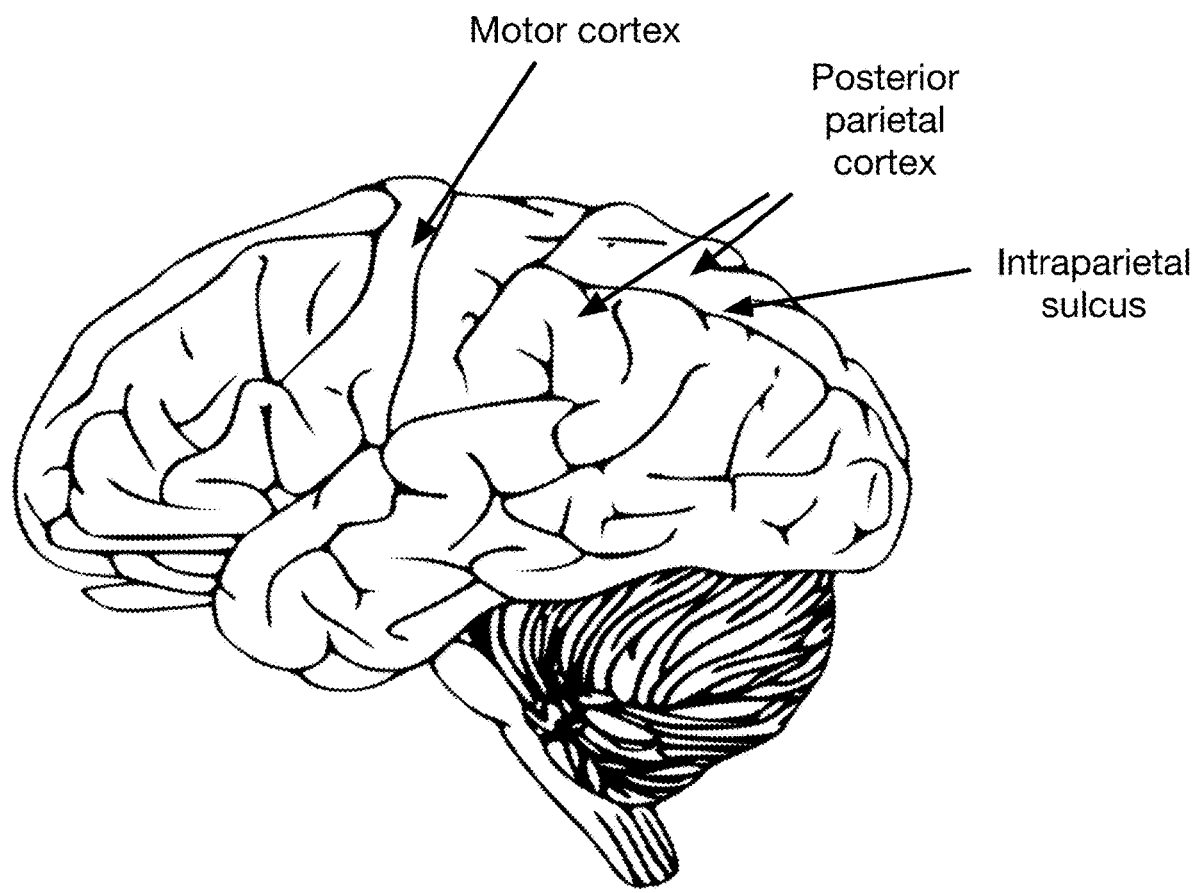
FIG. 8 represents a set of user brain regions.

In some variations, such as those involving a task of interest involving gaming, a set (e.g., subset) of electrodes are chosen which stimulate a posterior parietal cortex (PPC) (e.g., as shown in FIG. 8) region of the user. Stimulation of this region can be particularly advantageous for improving game play, as it has been shown to improve any or all of: visual attention (e.g., object-based attention, space-based attention, etc.), visuospatial judgments, spatial orienting, production of rapid decisions and plans for movements, target selection, coordinate transforms, integrating sensory and motor information, and interpreting other people's intentions by looking at their physical movements. In a specific example wherein the task of interest involves visual field search and covert visual orienting, the electrodes are placed such that an anode is arranged over the right PPC (P4 brain region and/or the left PPC (P3) brain region, and a cathode is arranged over the right deltoid muscle, wherein a stimulation pattern having a current amplitude between 1 and 2 milliamperes (mA) is applied for 20 minutes. In a second specific example, the electrodes are placed such that a first electrode is arranged over the right intraparietal sulcus (rIPS) brain region (e.g., as determined through fMRI) and a second electrode is placed over the left supraorbital cortex brain region. Cathodal stimulation of the rIPS at 2 mA can function to lower the ratio of distractor detection to target detection, which can help the user become better at recognizing a relevant target.

Additionally or alternatively, electrodes can be arranged proximal to any or all of the following brain and/or head regions: motor cortex, dorsolateral prefrontal cortex (DLPFC) (e.g., F3 region, F4 region, etc.) (e.g., as shown in FIG. 7), supraorbital regions (e.g., left supraorbital, right supraorbital, etc.), forehead regions, or any other suitable region.

In some variations, such as those involving an athletic task of interest, electrodes are stimulated proximal to a motor cortex region of the user.

In some variations, such as those involving cognitive goals such as mindfulness (e.g., concentration, focus, calm, etc.), creativity, improved working memory, multitasking ability, comprehension, verbal recall, language learning, etc., electrodes are stimulated proximal to the forehead of the user. In a specific example, a first electrode is arranged over a DLPFC region of the user and a second electrode is arranged over a supraorbital region of the user.

4.5 Method—Delivering Neurostimulation Pattern to User S250

Delivering the neurostimulation pattern to a user S250 functions to stimulate the prescribed regions of the user's brain, thereby improving user performance of the task of interest or accelerating improvement in user performance of the task of interest. In some variations, S250 includes operating a neurostimulation device according to the neuromodulation operation parameter values determined in S240. In some variations, the neurostimulation pattern improves performance of a task being performed as the stimulation is delivered. Additionally or alternatively, the neurostimulation pattern improves a future performance of the task of interest by increasing, for instance, the user's learnings from the task, the user's recall of the task, or any other features of the task.

The neurostimulation pattern is preferably applied contemporaneously with performance of the task of interest (e.g., concurrently, overlapping, during, etc.) but can additionally or alternatively be applied prior to performance of the task of interest, wherein the neurostimulation can serve as a priming session; after performance of the task of interest (e.g., to enhance user mood, to increase user calm, to increase consolidation of improvements, etc.); independently of a task of interest; or at any other suitable time.

In one variation, the neurostimulation pattern is delivered in response to an application 130 recommending the day's training program and the user selecting it (e.g., through a touch screen interface of the user device executing the application). The application 130 can communicate with the neurostimulation device to deliver stimulation. Additionally or alternatively, the user can interact with an interface of the neurostimulation device (e.g., set of dials, buttons, etc.) to initiate, adjust, or otherwise control the delivery of the neurostimulation pattern.

4.6 Method—Determining User Progress S260

The method can include determining user progress S260, which functions to assess the user's performance of the task of interest and/or the state of the user in relation to a task of interest. This can additionally function to inform the structure of a mapping, the contents of a stimulation pattern, or any other feature.

Figure 9B:
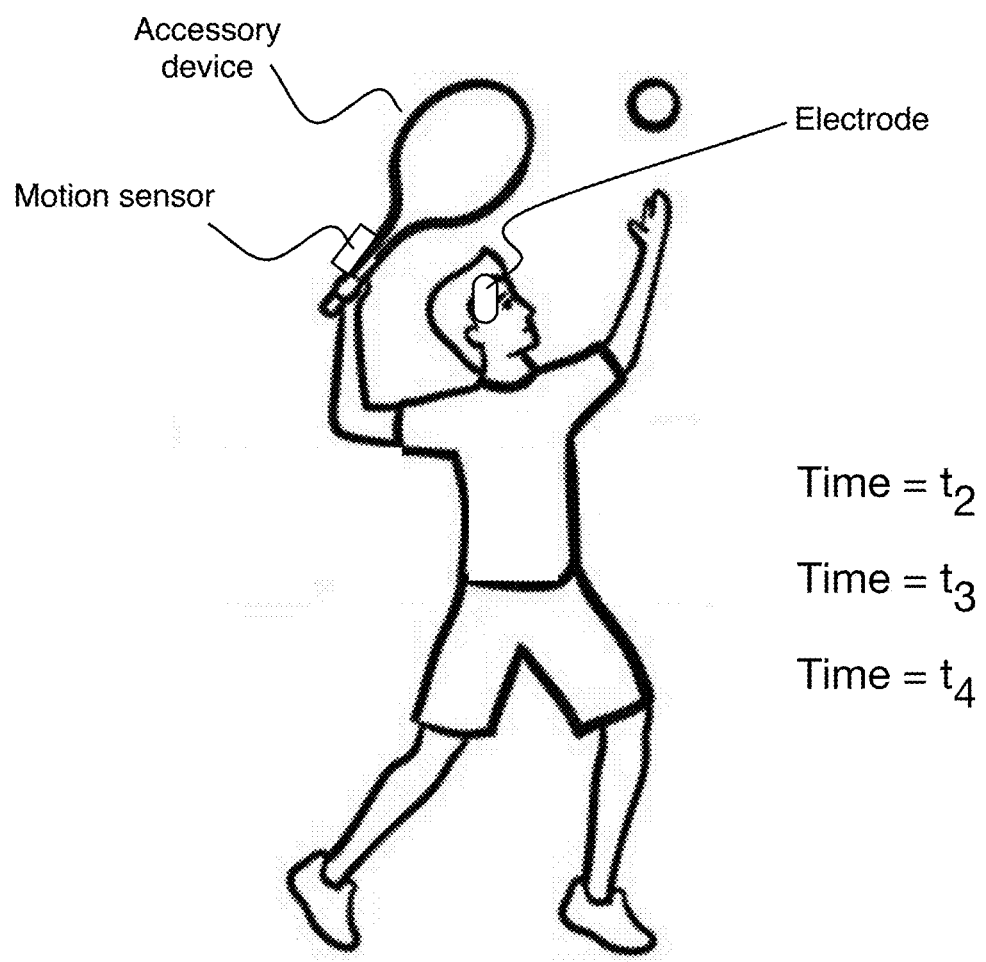
Figure 9C:
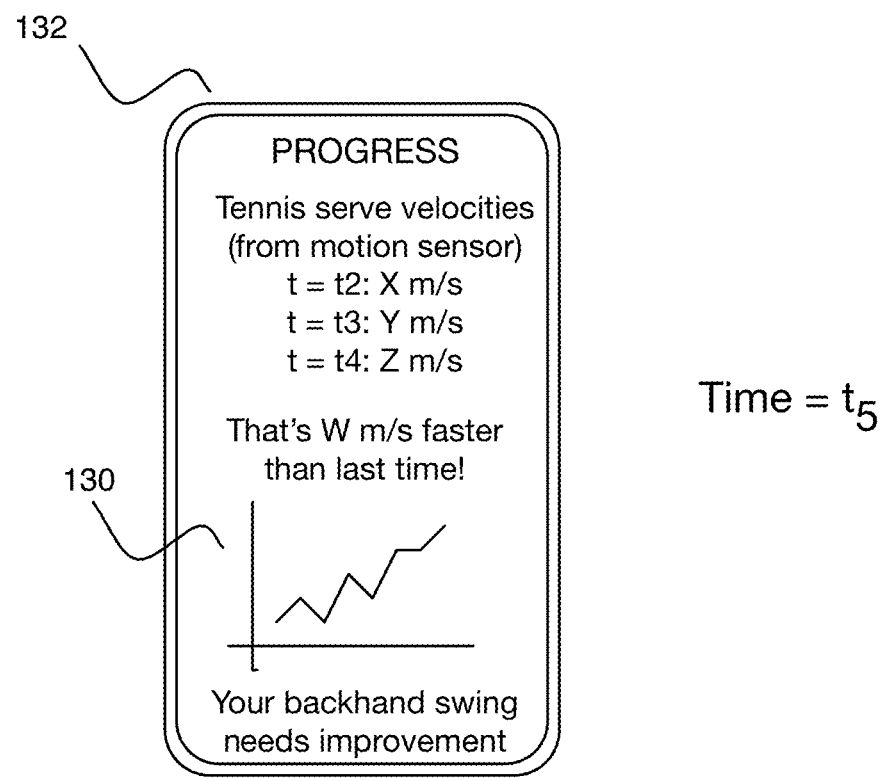

In preferred variations, S260 includes assessing performance of the task of interest (e.g., through determining a performance metric, though collecting a user score, etc.) and comparing with any or all of: a previous user performance of the task, a baseline performance, an aggregated user performance, an expected performance, or any other suitable metric. In specific examples, for instance, S260 can include collecting performance data and determining a user progress metric based on the performance data, which can include any or all of: collected sensor data (e.g., from a supplementary sensor, from an accelerometer on a golf club), measurements and/or scores from a game or cognitive training task (e.g., game provided through an application 130, athletic game, game provided at a separate device from the user device such as a video game, etc), physiological data (e.g., as measured from a biosignal sensor), data from an application program interface (API) of an accessory device (e.g., as shown in FIG. 9B) used during the performance of the task (e.g., video game controller, video game sports accessory, steering wheel, etc.), subjective user feedback, or any other suitable data.

In alternative variations, user progress can be determined (e.g., selected) solely by input (e.g., feedback in the form of a questionnaire) from the user, independent of a performance (e.g., based on a set of measured biosignals), predicted through a model or algorithm, or otherwise determined.

4.7 Method—Displaying User Progress S270

The method can include displaying user progress S270, which functions to inform the user of his performance of a task of interest and/or the progress the user has made in the task of interest, overall during his use of the neuromodulation device, or any other metrics. Additionally, S270 can function to prompt the user to provide feedback (e.g., indicating a satisfaction level with the progress, indicating a satisfaction level with the particular neurostimulation pattern, etc.).

User progress is preferably displayed at the application 130 (e.g., executing on user device) but can additionally or alternatively be displayed at a separate device (e.g., television, separate gaming application, etc.), not displayed (e.g., immediately stored in remote storage, etc.), or otherwise communicated.

User progress can be displayed through any or all of: a chart, plot, score, table, graph, graphic, rating, grade, or any other suitable display.

S270 is preferably performed in response to S260 but can additionally or alternatively be performed in response to a prompting of the user, during any suitable step of the method, multiple times throughout the method, or at any other time.

In one variation, user progress is displayed through a radial plot which indicates improvement in a first focus area of the task of interest. Additionally or alternatively, S270 can include displaying a focus area that needs further improvement, has not experienced progress, or is otherwise in need of further training.

4.8 Method—Receiving User Feedback S280

The method can optionally include receiving user feedback S280 at any time during the method, which can function to: assess the progress of the user, inform the selection of the task of interest, inform or adjust a mapping, determine a neuromodulation goal, or perform any other suitable function.

In some variations, S280 includes collecting user feedback during S260, wherein user progress is assessed at least partially based on the user feedback, such as through a user indication of a perceived performance during or after the task, a perceived outcome of the task, a comfort level associated with the stimulation, or any other indication. In some examples, an application 130 enables self-reporting and self-logging of user feedback. In a specific example, for instance, user progress is partially determined through a performance score collected through a game presented at an application 130, wherein the performance score is subsequently compared with a previous performance score. The user progress is then also partially determined by regular feedback collected at the same application 130, which indicates how the user feels regarding the performance and whether or not the user believes he is experiencing progress.

Additionally or alternatively, S280 can be performed after S270, wherein user feedback in response to displayed user progress (e.g., agreement with displayed progress, disagreement with displayed progress, etc.) is used to adapt the neuromodulation program in future iterations.

4.9 Method—Adapting Neuromodulation Program Based on Progress and/or Feedback S290

The method can include adapting a neuromodulation program (e.g., previously performed neuromodulation program, future neuromodulation program, etc.) and/or a mapping based on user progress and/or user feedback S290, which can function to adjust the neuromodulation program and/or one or more mappings based on one or more learnings from the method 200. The neuromodulation program can be adapted for a single user (e.g., user who performed a task of interest, user who provided feedback, etc.), a plurality of users (e.g., all users having the same neurostimulation device, all users indicating the same task of interest, etc.), or any other set of individuals. Instead of adapting an existing neuromodulation program, a new neuromodulation program can additionally or alternatively be determined during S290.

In some variations, adapting the neuromodulation pattern includes adjusting one or more parameters of the neurostimulation pattern, such as, but not limited to: a current amplitude, an electrode selection, a stimulation pattern duration, or a stimulation pattern schedule (e.g., reducing the number of times a particular stimulation pattern is applied per week, increasing the number of times a particular stimulation pattern is applied per week, etc.). The neurostimulation pattern can be adjusted and stored for a future application of the neurostimulation pattern; additionally or alternatively, however, a neurostimulation pattern can be adjusted as it is being applied (e.g., user does not feel expected effects and wants to bump up the amplitude of the current). The neurostimulation pattern can be adjusted: according to a predetermined set of rules (e.g., wherein a specific new stimulation pattern is selected when the user feedback is negative; increasing the stimulation pattern schedule when the sensor signals indicate that the user is not progressing based on a target progression; etc.), randomly adjusted, iteratively adjusted, or otherwise adjusted. The neurostimulation pattern can be adjusted until a neurostimulation target (e.g., for the task and goal combination) are met, until the user feedback is positive, until the sensor signals indicative of user performance indicate that the neurostimulation target is substantially met (e.g., when the signal patterns match, when the signals are classified as matching the target, etc.), or until any other suitable condition is met.

Additionally or alternatively, mapping matrices and neuromodulation programs can be adjusted or determined based on aggregated data, clinical data, research, academic publications, or any other suitable information.

In one variation, a mapping matrix is adjusted in response to determining through the user progress that a neuromodulation goal has been prioritized, wherein adjusting the mapping matrix includes deprioritizing the mastered goal and selecting a new goal for future iterations of the method 200.

In a second variation, a neuromodulation program is adapted based on sensor data and user-reported feedback, wherein the neuromodulation program is adapted to deliver additional or otherwise modified stimulation in areas where progress is slower based on a predefined table.

4.10 Method—Variations

In one variation, the method 200 includes: querying a user regarding his interests and goals through a mobile application 130; receiving user feedback at the application 130 indicating that the user has an interest in tennis and a perceived expert-level ability; accessing a mapping (e.g., database, predefined table, table individualized or adapted to by a coach in communication with the user) through the application and/or a remote server; retrieving, at the application 130, a set of prioritized neuromodulation goals appropriate to that task and skill level (e.g., reading and recognition of an opponent's movements and ball movements as a first priority and fine-tuning of dominant hand motor skill as a second priority); determining from the mapping a neuromodulation target, waveform, and stimulation training program for each goal (e.g., for movement recognition: anodal, cathodal, or random noise stimulation applied to the posterior intraparietal sulcus (PIPS) at 2 mA for 20 minutes twice a week while viewing and responding to video of tennis serves as well as random noise stimulation at 0.25 mA root mean square current applied to the left primary motor cortex hand region while practicing a backhand stroke for 30 minutes once per week); reminding the user to perform his scheduled neuromodulation program with mobile (e.g., text message) or email reminders; recommending the day's training program to the user through the application 130 and receiving the user's selection; communication the neuromodulation program to the neuromodulation device 110 from the application 130; collecting performance data at the application 130 through any or all of: user input, an API of a video serve game, and an accelerometer embedded in a tennis racket, and comparing the performance data with expected performance; prompting the user through the application 130 to provide feedback after the neuromodulation program; displaying a radial plot to the user at the application indicating an improvement in backhand stroke but not in serve recognition; providing at the application 130 guidance and information from a coach who is reviewing the user's performance data on a regular basis; adjusting the initial recommendation to become motor cortex stimulation once per two weeks and a different polarity of PIPS stimulation three times per week; connecting the user with other users in a community (e.g., tennis community) with the same skill level and goals to exchange ideas and support (e.g., through the application 130); and enabling the user to share progress (e.g., in response to achieving a milestone) with other users, social media, or any other platform.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method for providing individualized neurostimulation to a user through a neurostimulation device, the method comprising:
   at an application executing on a user device:
      receiving an input from the user associated with a program at the application;
      determining a neuromodulation goal based on the program, wherein the neuromodulation goal is determined at least in part with a first mapping;
      determining an individualized neurostimulation pattern with a second mapping, wherein the neurostimulation pattern is configured to achieve the neuromodulation goal;
   at the neurostimulation device, delivering the neurostimulation pattern;
   at the application:
      calculating a user progress metric associated with the neuromodulation goal; and
      updating the neurostimulation pattern based on the user progress metric.

2. The method of claim 1, wherein the program is a mental health program.

3. The method of claim 1, wherein the input from the user comprises a selection of an exercise in the program.

4. The method of claim 1, further comprising determining a user experience level associated with the program, wherein the neuromodulation goal is further determined based on the user experience level.

5. The method of claim 4, wherein the user experience level associated with the program is determined based on historical information associated with the user and the application.

6. The method of claim 5, wherein determining the user experience level associated with the program comprises retrieving a prior user progress metric.

7. The method of claim 1, wherein the second mapping comprises a lookup table.

8. The method of claim 1, wherein the application further comprises a messaging platform configured to transmit a set of messages to the user and receive feedback from the user.

9. The method of claim 8, wherein the neurostimulation pattern is further determined based on information from the messaging platform.

10. The method of claim 8, wherein the neurostimulation pattern is further updated based on information from the messaging platform.

11. The method of claim 1, wherein updating the neurostimulation pattern comprises updating at least one of: a set of locations at which the neurostimulation pattern is applied, a waveform of the neurostimulation pattern, and an intensity of the neurostimulation pattern.

12. The method of claim 1, wherein the neurostimulation pattern comprises a waveform having at least one of: a theta-band component and a gamma-band component.

13. A system for providing individualized neurostimulation to a user, the system comprising:
a neurostimulation device comprising a set of electrodes, wherein the neurostimulation device is configured to deliver a neurostimulation pattern to a head region of the user through the set of electrodes;
an application configured to execute on a user device; and
a computing system in communication with the application, wherein the computing system:
receives an input from the user associated with a program at the application;
determines a neuromodulation goal associated with the user based on the program and a first mapping;
determines an individualized neurostimulation pattern with a second mapping, wherein the individualized neurostimulation pattern is configured to achieve the neuromodulation goal;
transmits the neurostimulation pattern to the neurostimulation device;
calculates a user progress metric associated with the neuromodulation goal and in response to the neurostimulation pattern; and
updates the neurostimulation pattern based on the user progress metric.

14. The system of claim 13, wherein the application further comprises a messaging platform, wherein the individualized neurostimulation pattern is further determined based on information from the messaging platform.

15. The system of claim 13, wherein the computing system is further configured to determine a user experience level associated with the program, wherein the neuromodulation goal is further determined based on the user experience level.

16. The system of claim 13, wherein at least a portion of the computing system is arranged onboard the user device.

17. The system of claim 16, wherein at least a portion of the computing system is arranged remote from the user device.

18. The system of claim 13, wherein the set of electrodes comprises multiple electrodes arranged at a forehead region of the user, wherein updating the neurostimulation pattern comprises determining an updated subset of the set of multiple electrodes, wherein the neurostimulation device delivers the updated neurostimulation pattern through the updated subset.

19. The system of claim 18, wherein the set of multiple electrodes is at least partially arranged at a forehead region of the user.

20. The system of claim 13, wherein the input from the user comprises a selection of a mental exercise in the program.

* * * * *